United States Patent [19]
Snable

[11] Patent Number: 6,162,428
[45] Date of Patent: *Dec. 19, 2000

[54] HNT-NEURON HUMAN NEURONAL CELLS TO REPLACE GANGLION CELLS

[75] Inventor: Gary L. Snable, Atherton, Calif.

[73] Assignee: Layton Bioscience, Inc., Sunnyvale, Calif.

[*] Notice: This patent issued on a continued prosecution application filed under 37 CFR 1.53(d), and is subject to the twenty year patent term provisions of 35 U.S.C. 154(a)(2).

[21] Appl. No.: 08/800,224

[22] Filed: Feb. 12, 1997

[51] Int. Cl.$^7$ .............................. A01N 63/00; C12N 5/08
[52] U.S. Cl. ...................... 424/93.1; 424/93.21; 435/325
[58] Field of Search .................................. 424/93.1, 93.2, 424/93.21; 435/325

[56] References Cited

U.S. PATENT DOCUMENTS 5,175,103  12/1992  Lee et al. .............................. 435/172.3

OTHER PUBLICATIONS

Rapp, L. M. Retinal Phototoxicity. Handbook of Neurotoxicity. Macel Dekker, Inc., pp. 963–1003, 1995.

Jackowski, A. Neural injury repair: hope for the future as barriers to effective CNS regeneration become clearer. British Journal of Neurosurgery, vol. 9, pp. 303–317, 1995.

Cerro et al., "Neural Retinal Transplantation into 12 RP Patients." Invest. Ophthal. Vis.Sci. 38(4):S261, 1997.

DiLoreto, Cerro and Cerro, "Cyclosporine treatment promotes survival of human fetal neural retina transplanted to the subretinal space of light–damaged fischer 344 rat." Experimental Neurology 140:37–42, 1996 (Jul.).

Honjo et al., "Estrogen as a growth factor to central nervous cells." Steroid Biochem. Molec. Biol. 41(3–8):633–635, 1992.

Olson et al., "Conditions for adrenergic hyperinnervation in hippocampus: histochemical evidence from intraocular double grafts." Exper. Brain Res. 39:277–88, 1980.

Little et al. "Transplantation of Human Fetal Retinal Pigment Epithelium Rescues Photoreceptor Cells From Degeneration in the Royal College of Surgeons Rat Retina." Invest Ophthalmol Vis Sci 37:204–11, 1996.

Aramant and Seiler, "Fiber and Synaptic Connections Between Embrionic Retinal Transplants and Host Retina." Experimental Neurology 133:244–55, 1995.

Castillo BV et al. "Efficacy of Nonfetal Human RPE for Photoreceptor Rescue: A Study in Dystrophic RCS Rats." Experimental Neurology 146(1):1–9, 1997.

Trojanowski et al. "Neurons from Human Teratocarcinoma Cell Line." ExperimNeurol 122:283–94, 1993.

Gutin et al., "Recurrent malignant gliomas: survival following interstitial brachytherapy with high–activity iodine–125 sources." J. Neurosurg 67:864–73, 1987.

Couldwelland Apuzzo. "Initial experience related to the use of the Cosman–Roberts–Wells stereotactic instrument." J. Neurosurg 72:145–48, 1990.

*Primary Examiner*—Deborah J. Clark
*Attorney, Agent, or Firm*—Barbara J. Luther

[57] ABSTRACT

Disclosed herein is the treatment of vision loss in a mammal by transplanting an effective amount of hNT-Neuron cells. The treatment can be accomplished by injecting the cells into the retinal area of the eye. Additionally, the cells can be injected into the visual cortex of the brain. Conditions to be treated are vision loss due to optic nerve damage, including glaucoma, optic nerve sheath meningioma and glioma, Graves' ophthalmopathy, benign or malignant orbital tumors, metastatic lesions, tumors arising from the adjacent paranasal sinuses or middle cranial fossa, giant pituitary adenomas, brain tumors or abscesses, cerebral trauma or hemorrhage, meningitis, arachnoidal adhesions, pseudotumor cerebri, cavernous sinus thrombosis, dural sinus thrombosis, encephalitis, space-occupying brain lesions, severe hypertensive disease or pulmonary emphysema.

9 Claims, 12 Drawing Sheets

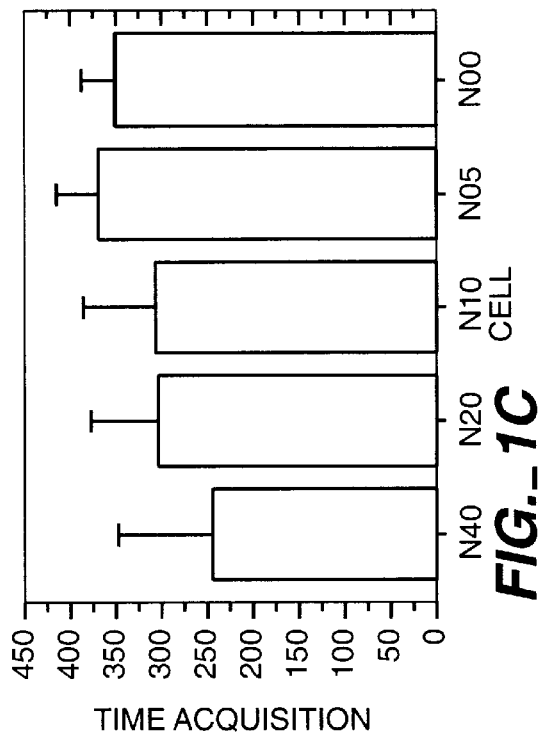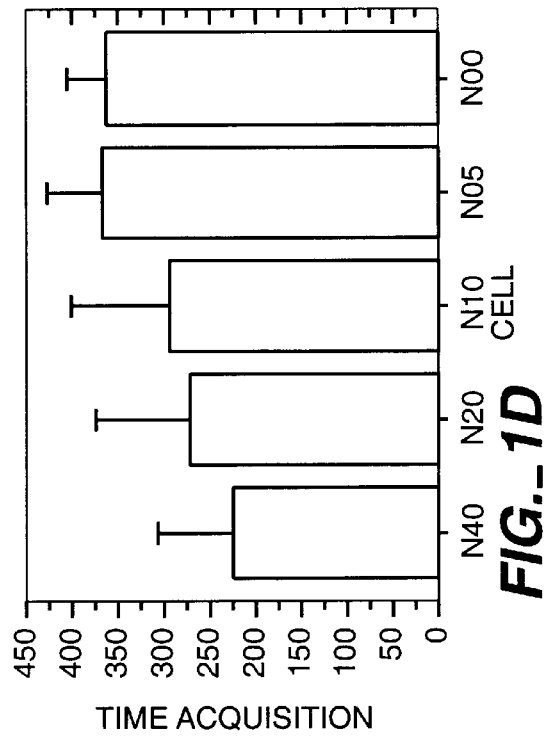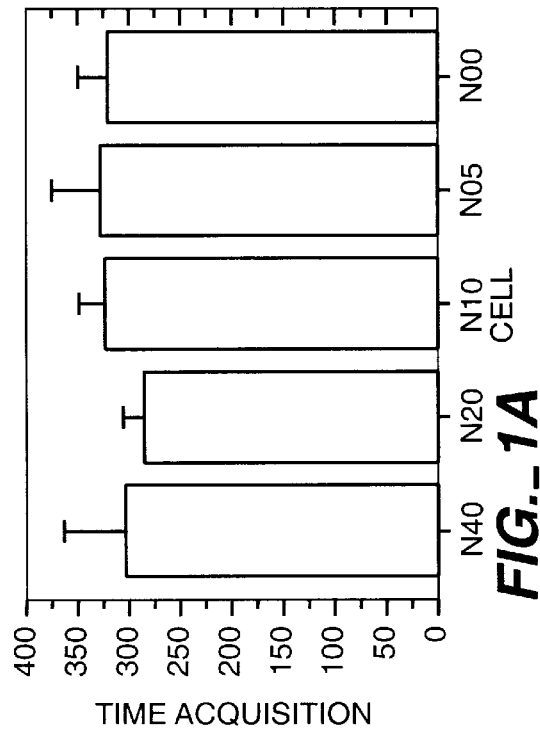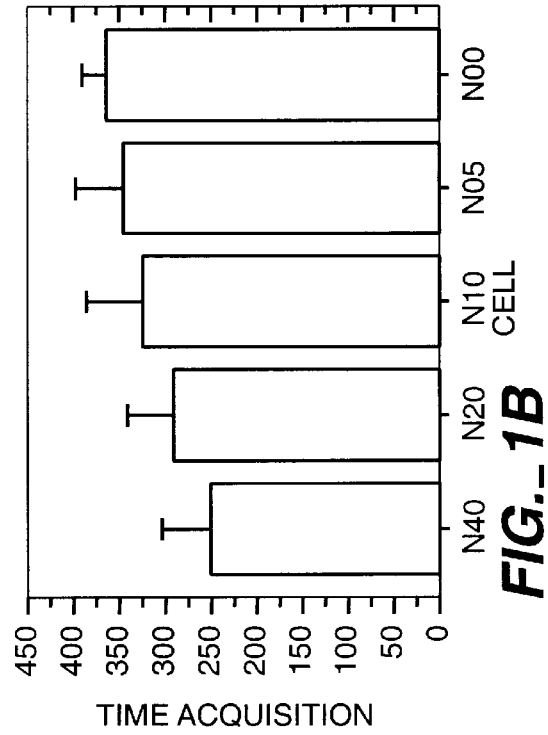

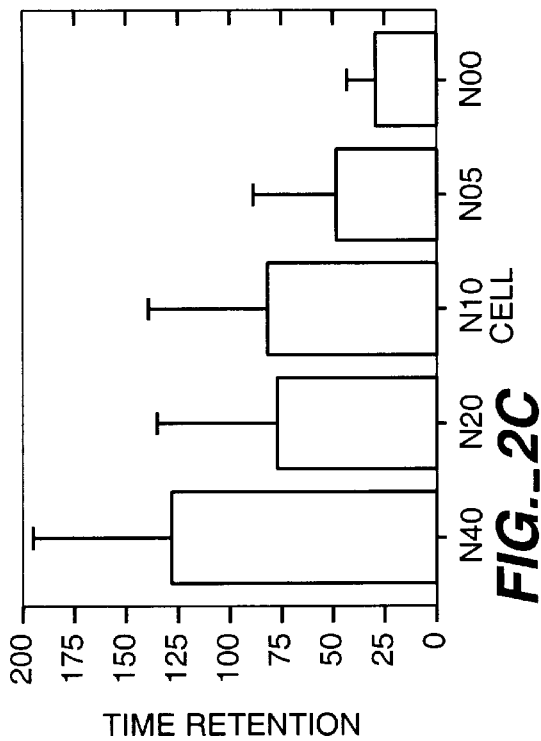
FIG._2A
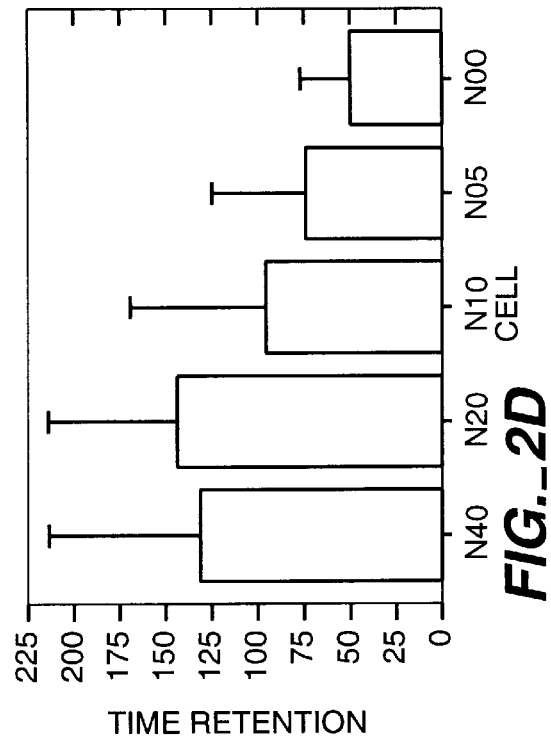
FIG._2B
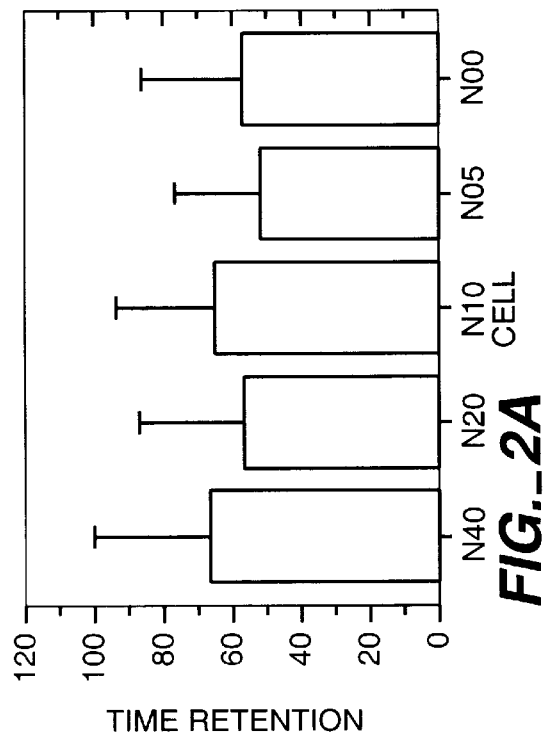
FIG._2C
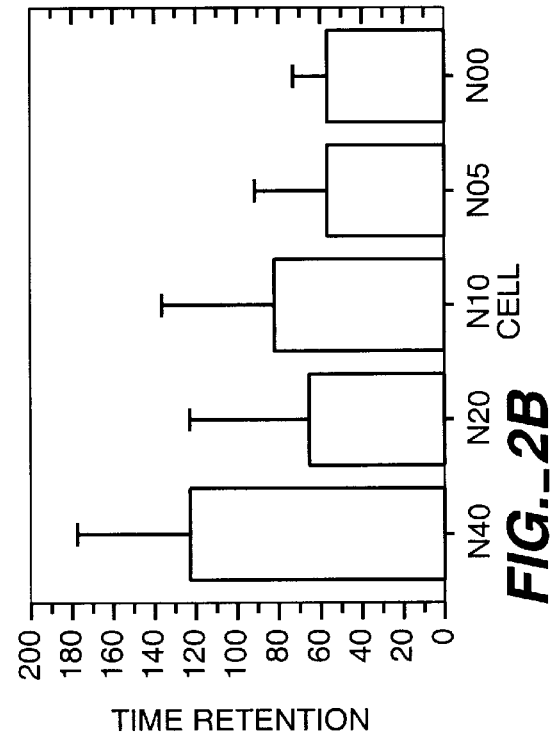
FIG._2D

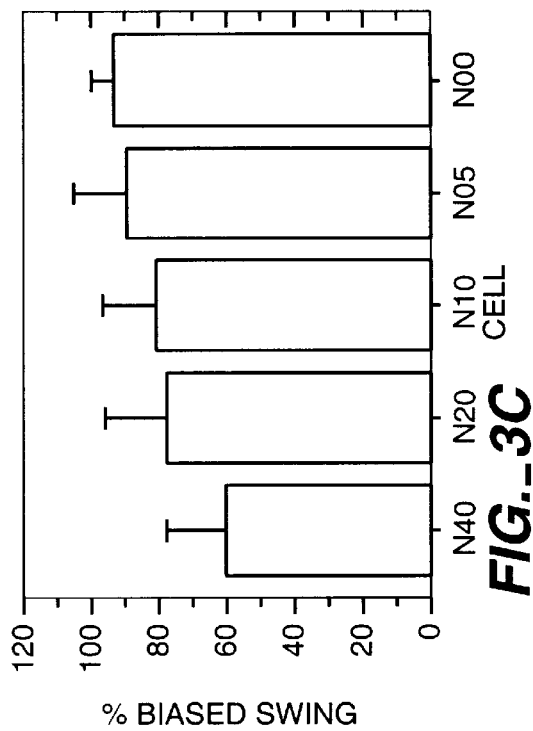
FIG._3A
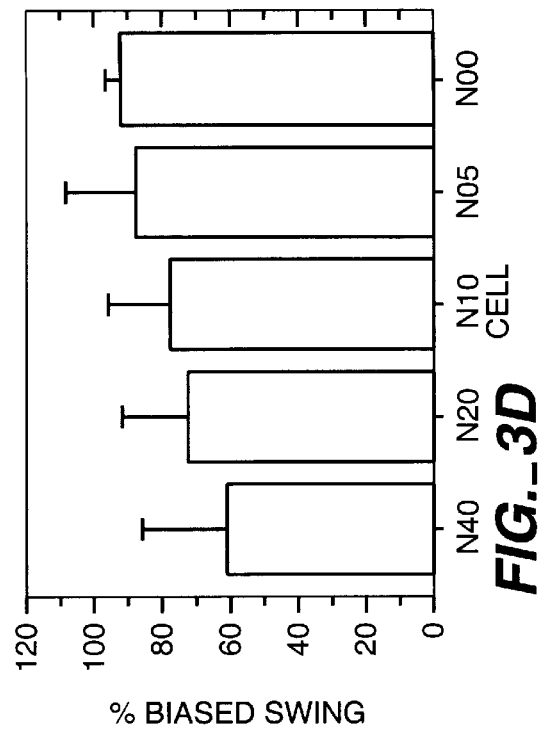
FIG._3B
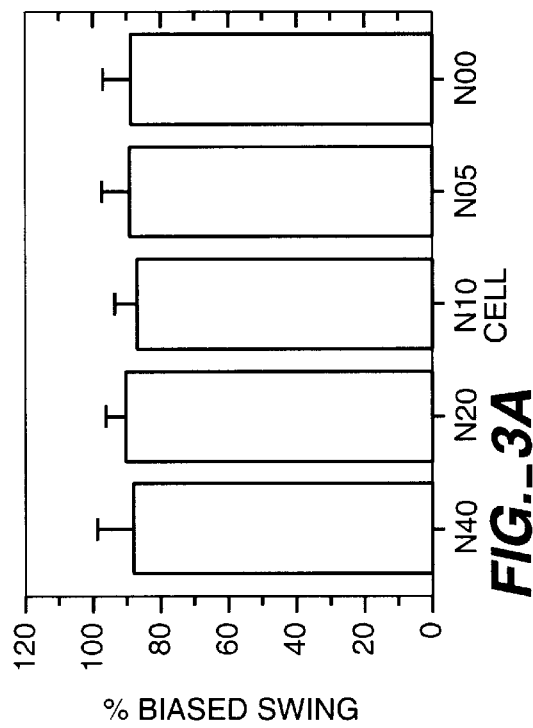
FIG._3C
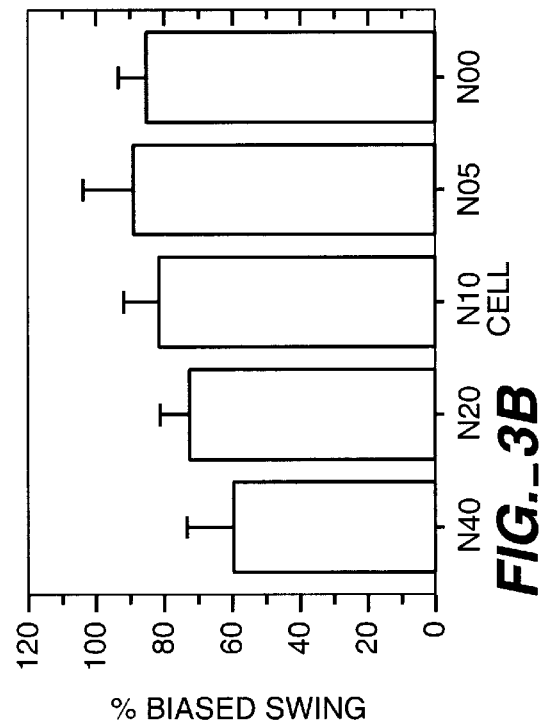
FIG._3D

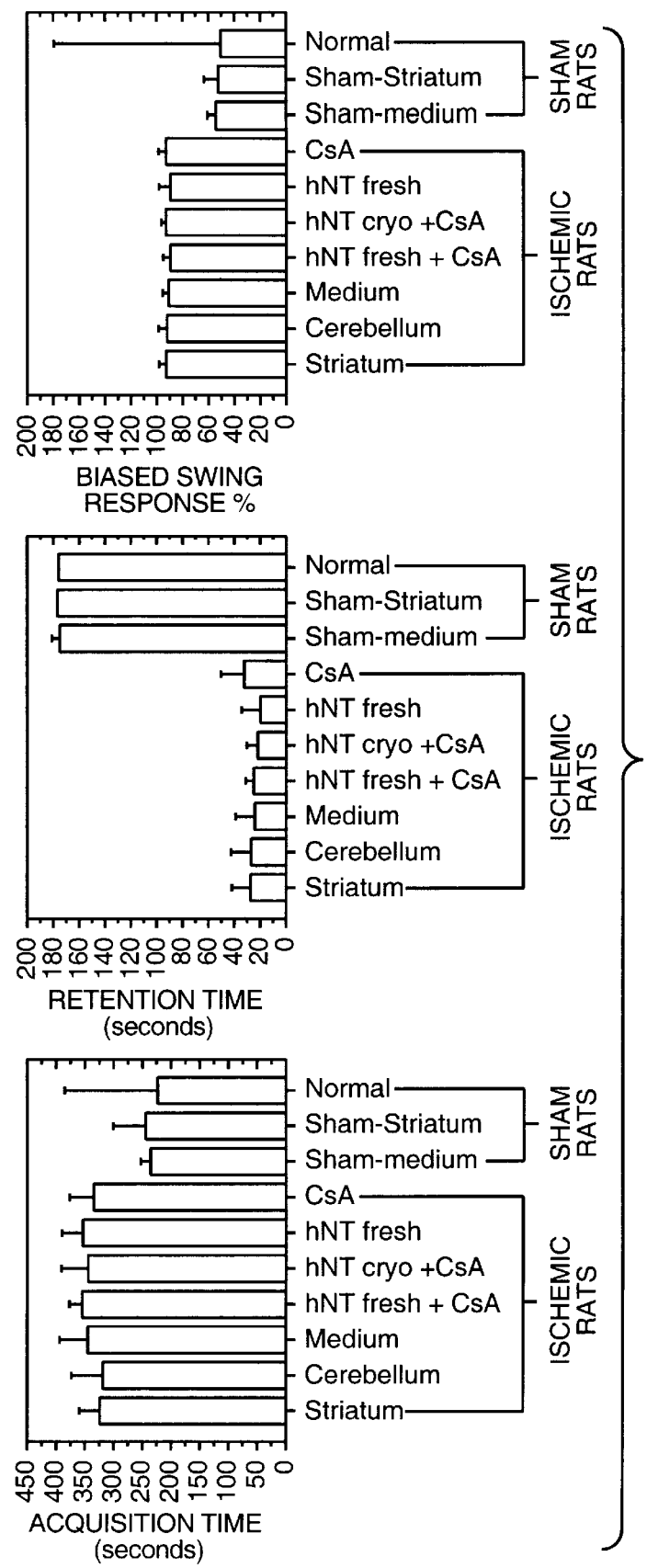
FIG._4

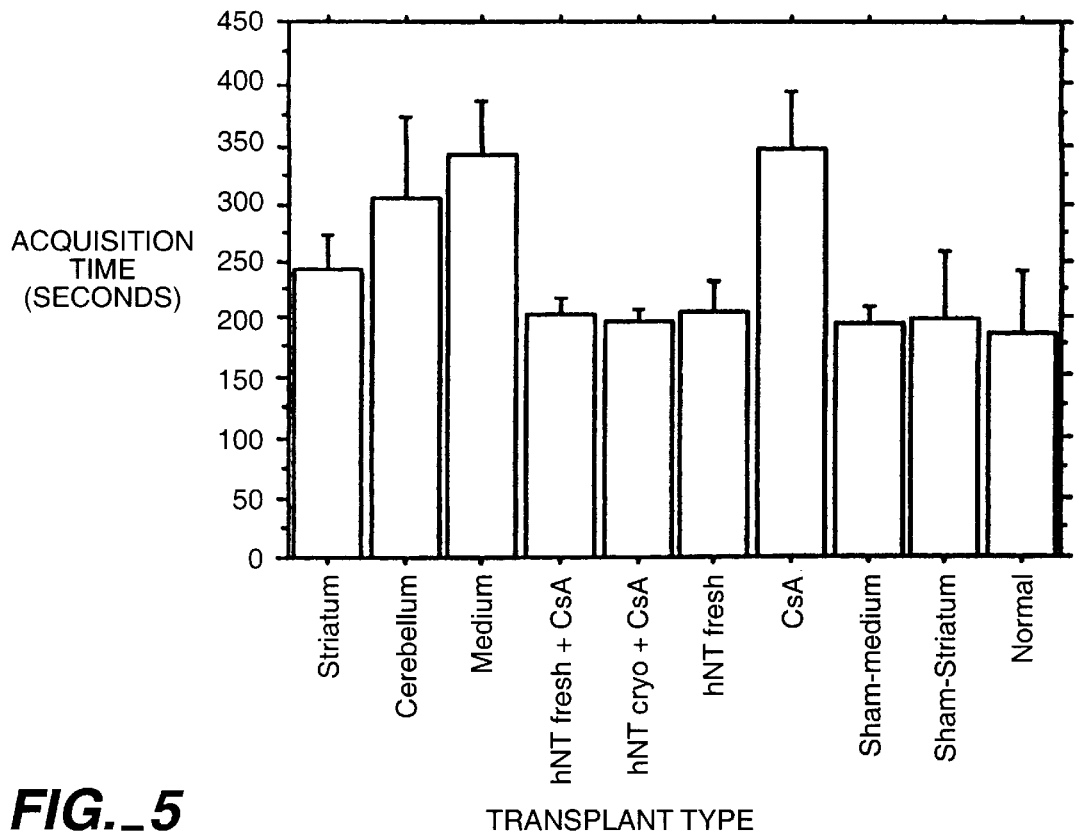
FIG._5
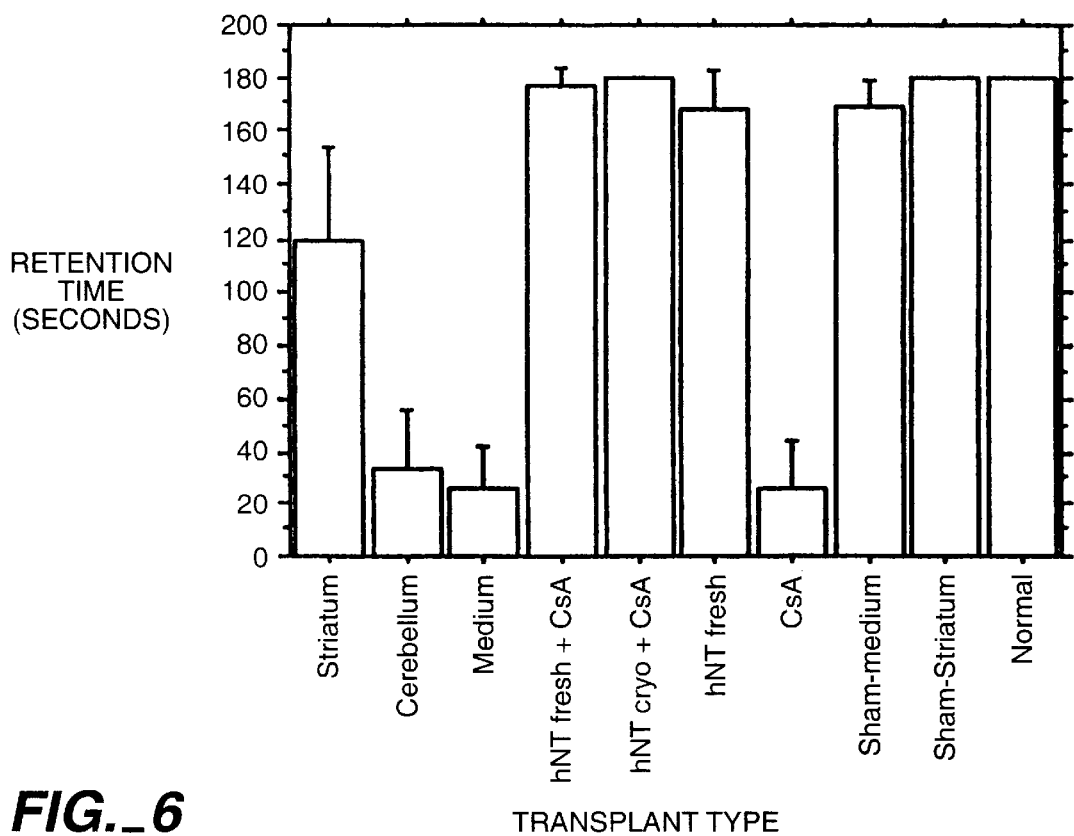
FIG._6

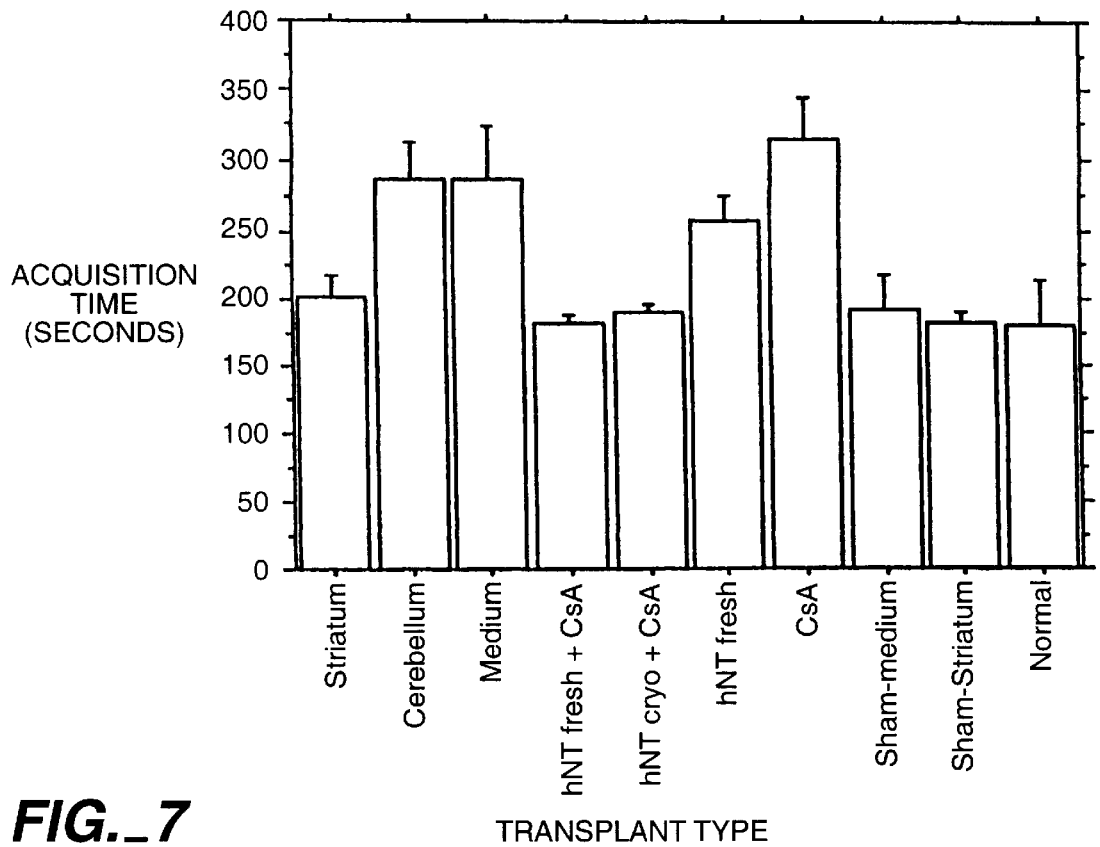
FIG._7
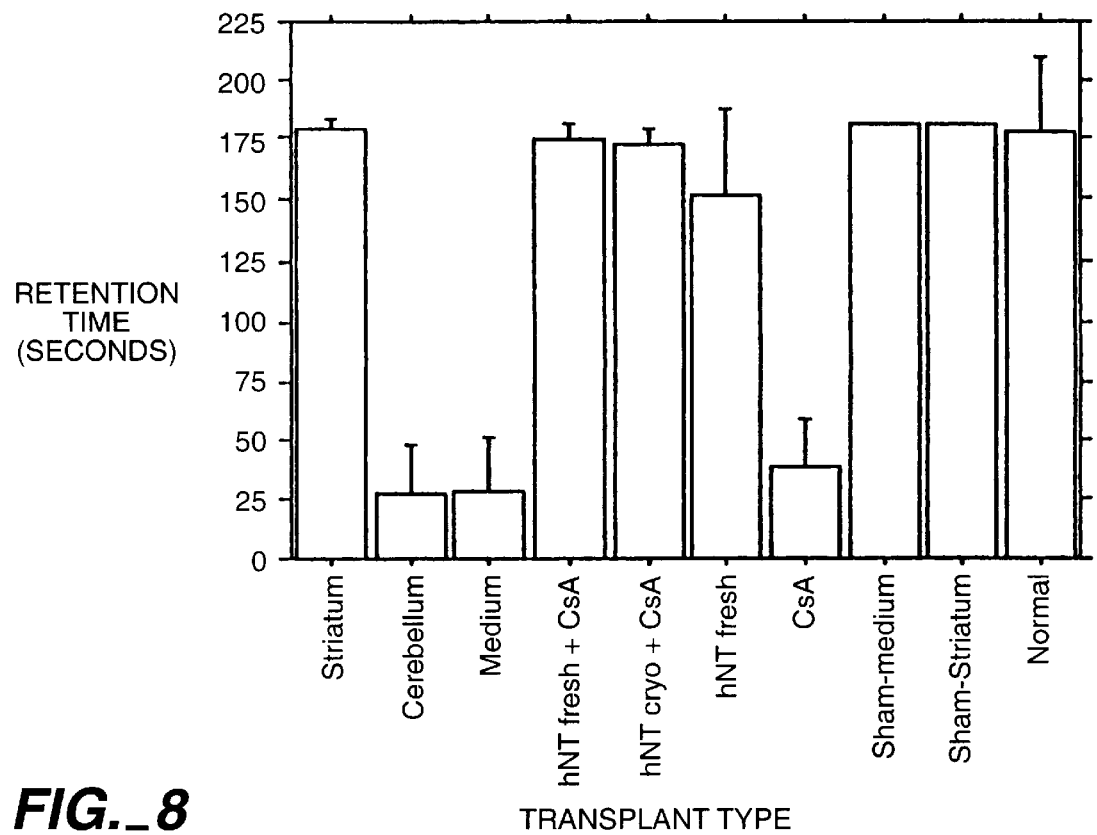
FIG._8

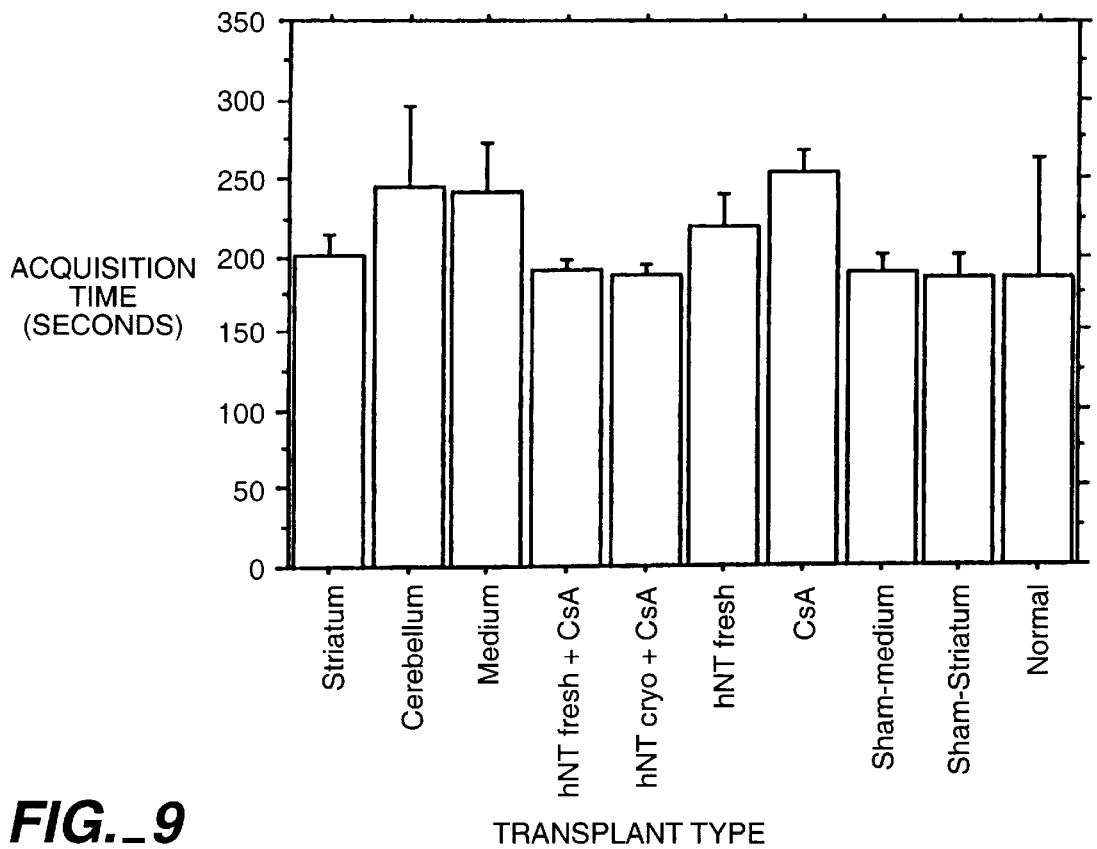
FIG._9
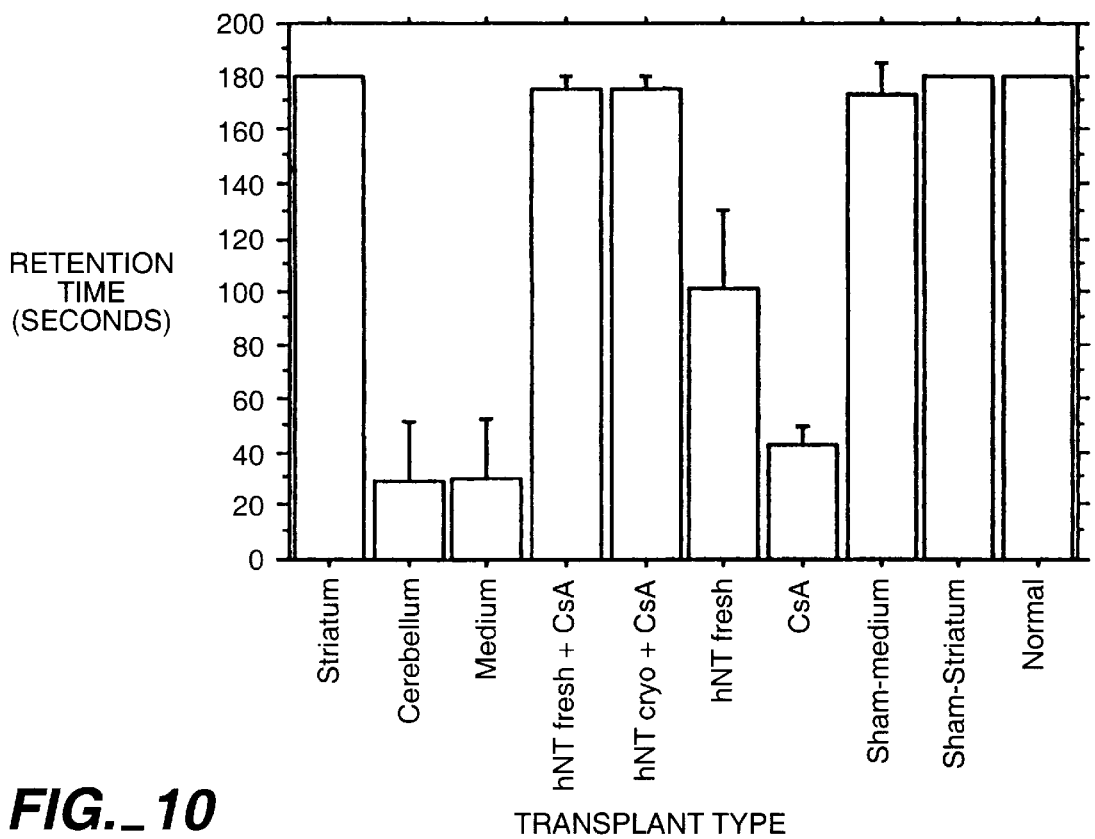
FIG._10

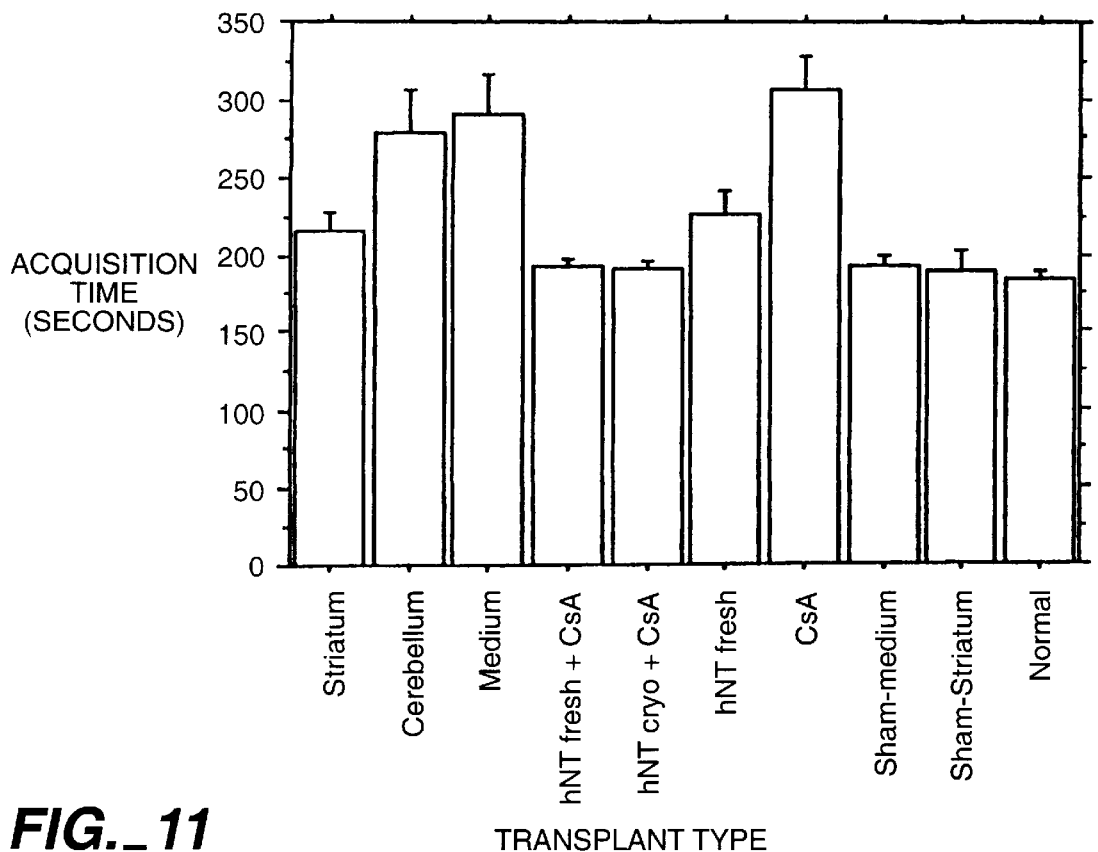
FIG._11
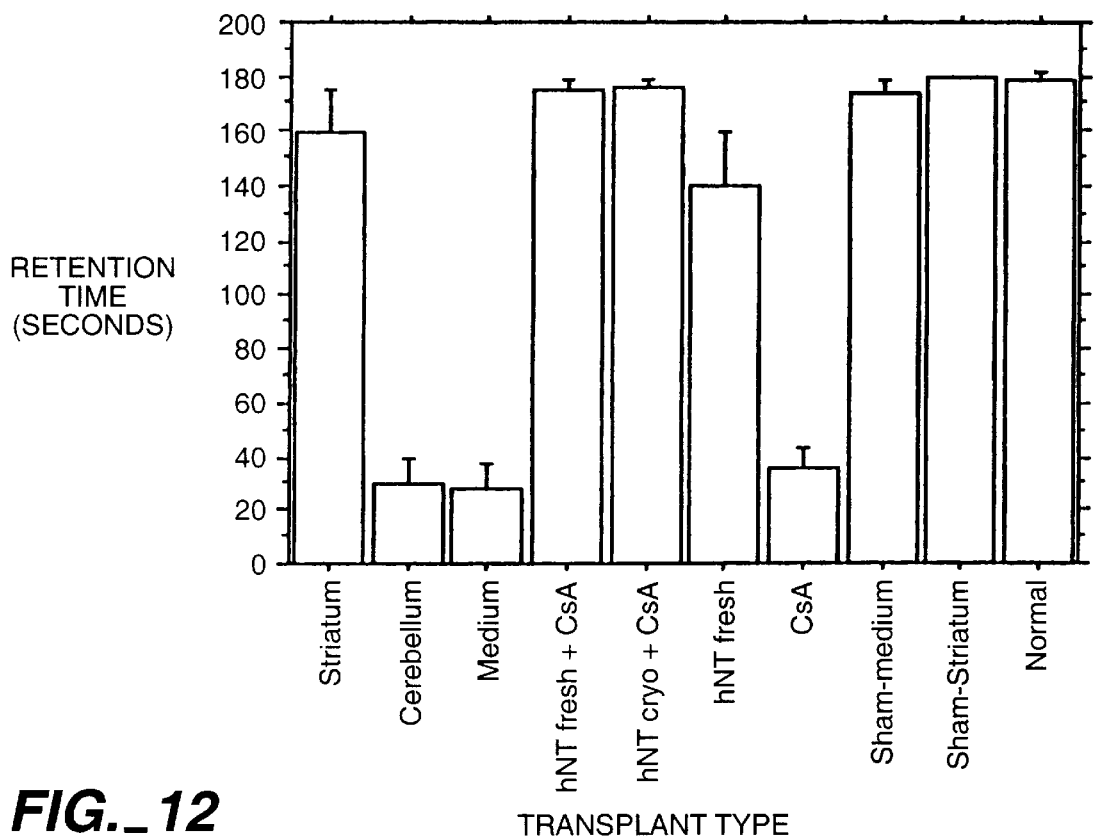
FIG._12

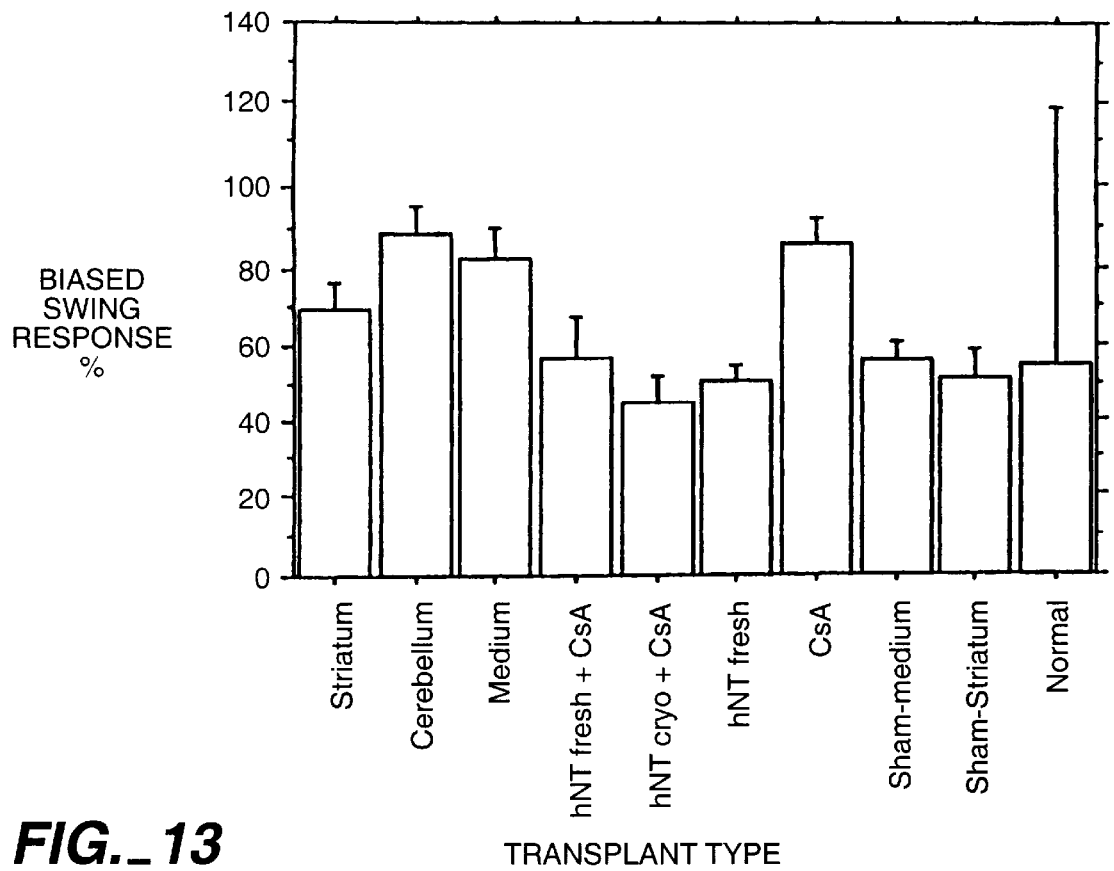
FIG._13
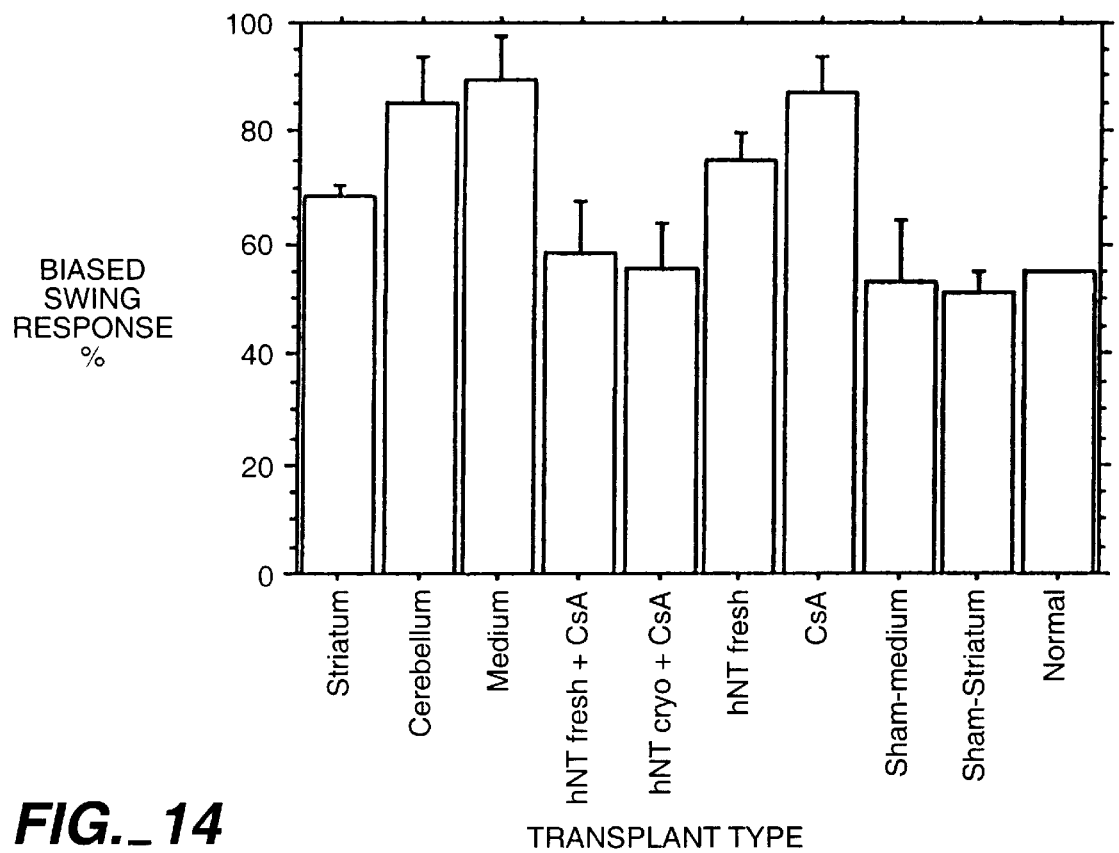
FIG._14

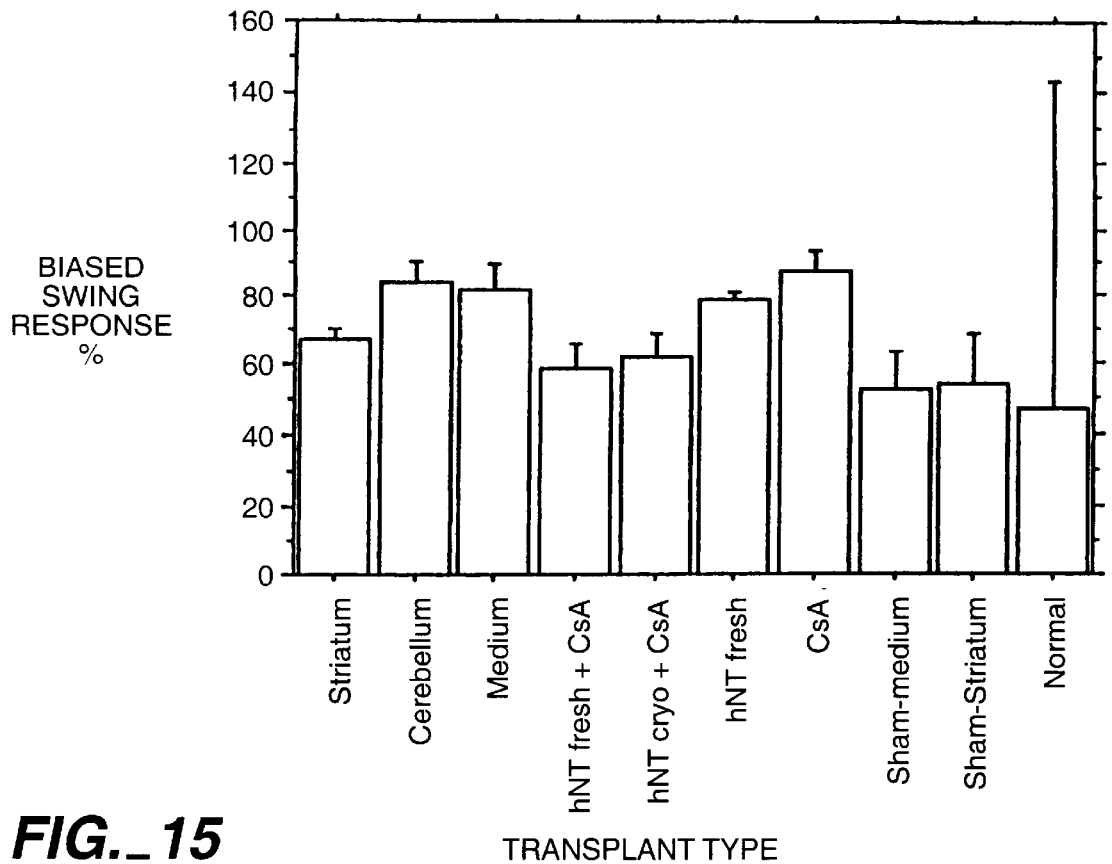
FIG._15
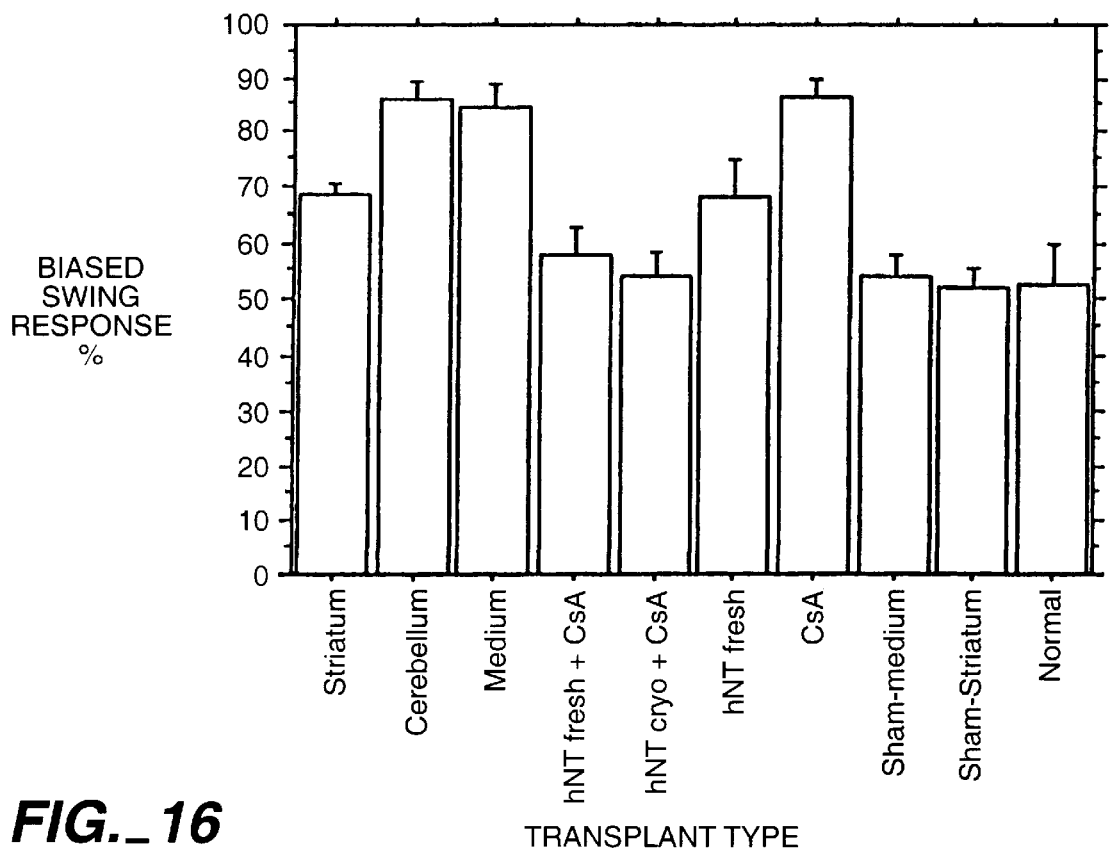
FIG._16

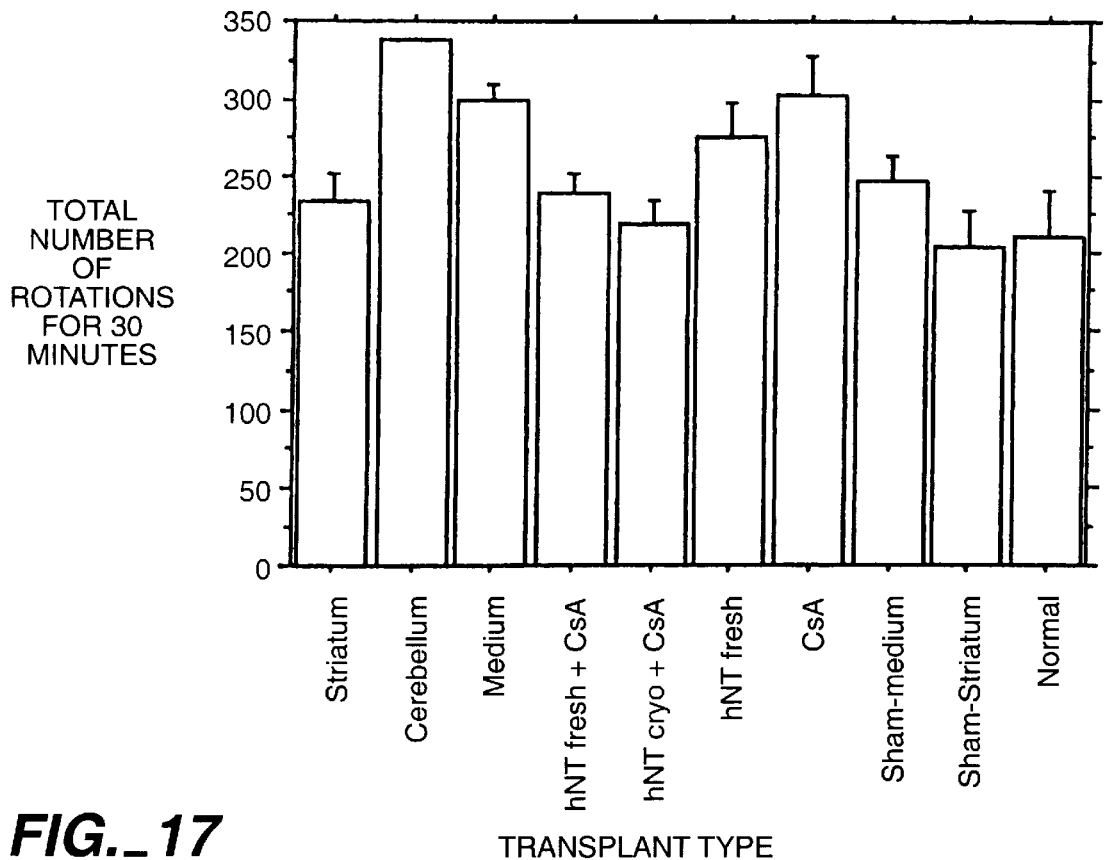
FIG._17
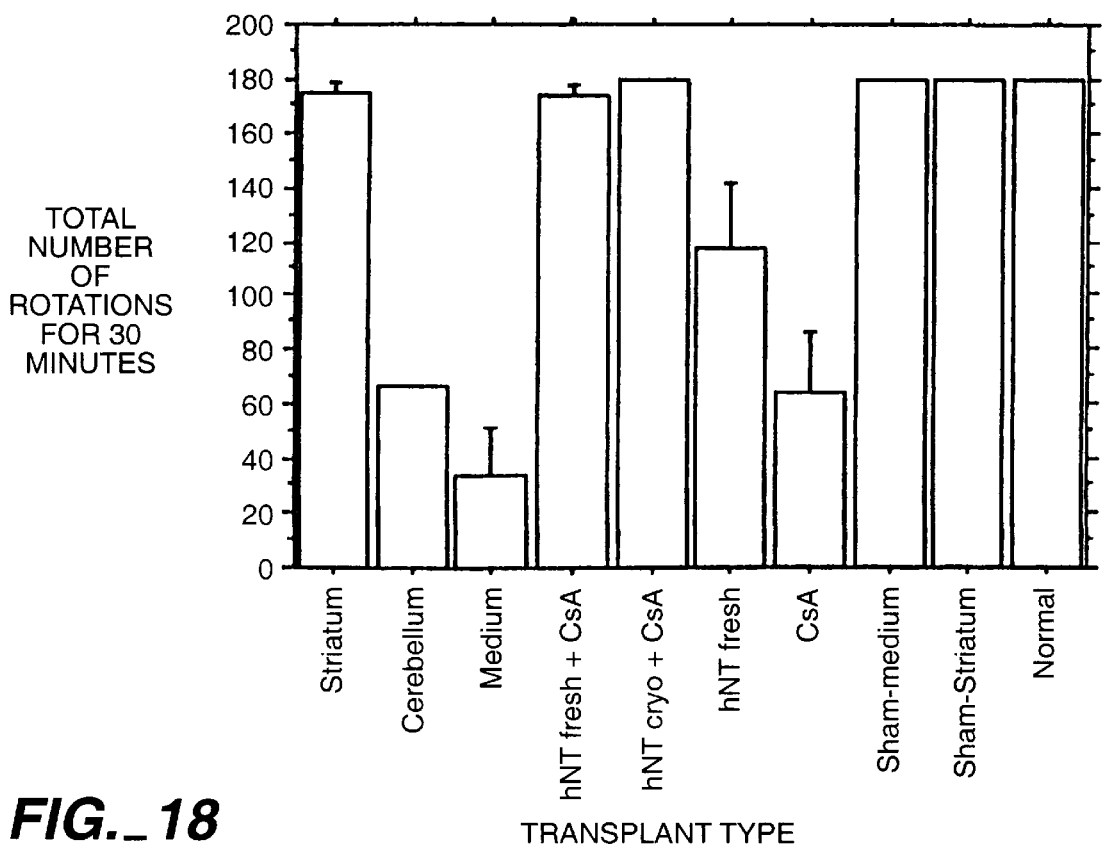
FIG._18

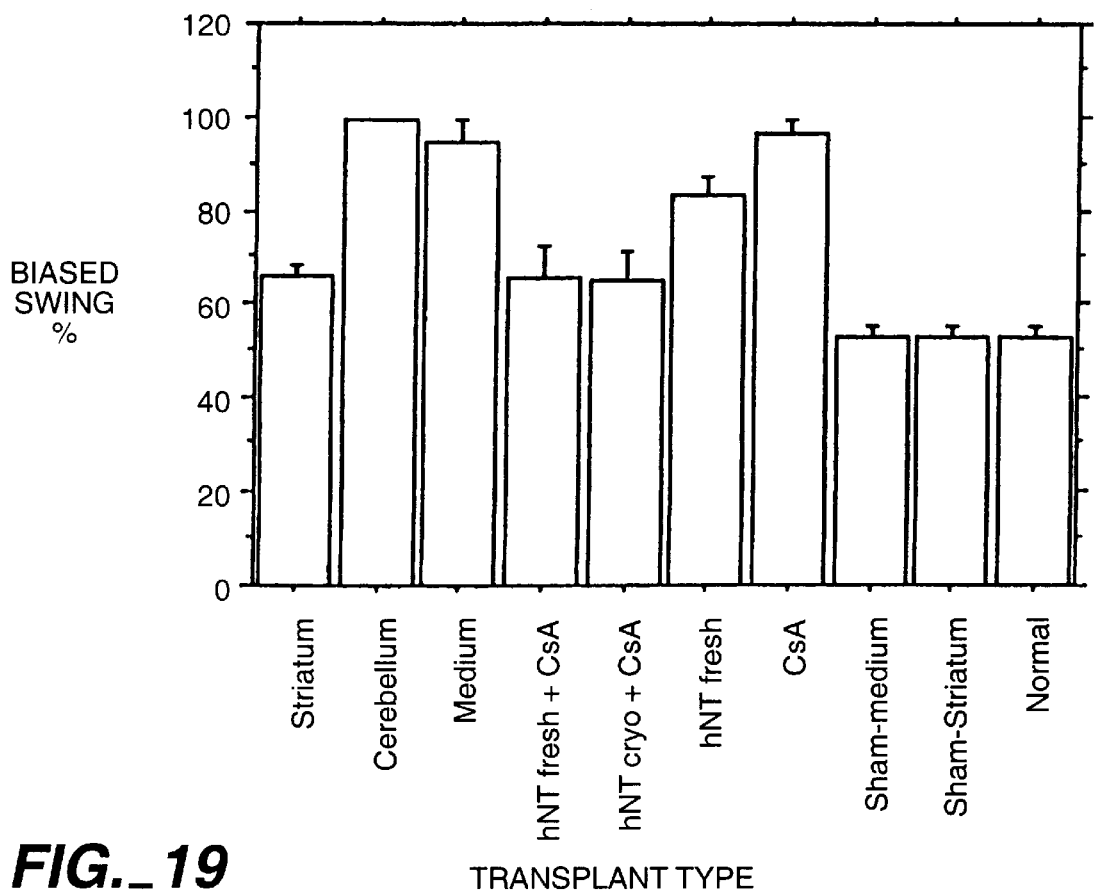
FIG._19

HNT-NEURON HUMAN NEURONAL CELLS TO REPLACE GANGLION CELLS

FIELD OF USE

The present invention is in the field of human transplantation and more particularly in the field of intraocular and intracranial transplantation of specially treated human cells which reestablish neuronal connections between the retina and the ocular cortex, which neurons having been damaged by glaucoma or other compression-causing injuries and diseases.

BACKGROUND INFORMATION

Glaucoma is the occurrence of elevated intraocular pressure which causes progressive blindness in the form of gradual loss of peripheral fields of vision. It is an important cause of blindness and occurs in 1–2% of individuals over the age of 60. Often the disease is asymptomatic, as the patient painlessly and gradually loses vision. Before a diagnosis is made, the patient may have lost half of the one million optic nerve fibers in one eye. Today, intervention is focused on early detection, which depends on a routine eye examination which includes intraocular pressure measurement (tonometry), funduscropy with attention to the optic disc appearance, and visual field testing. In the normal eye, the optic cups are symmetric and the neural rim is pink. In glaucoma, either localized notching or generalized enlargement of the optic cup can be seen. The rim, although thinned, remains pink until late in the disease. The central optic cup diameter can be compared with the diameter of the disc. The ratio of the horizontal and vertical dimensions can be recorded. The normal cup-disc ratio is less than 0.2 to 0.3. Vertical disparity in one or both eyes is an early sign of glaucoma.

Glaucoma is often asymmetric. The finding of asymmetry of the cup-disc ratio implies glaucoma. Early in the disease, visual field loss may include nonspecific constriction and small paracentral scotomas. Eventually, the arcuate nerve fiber bundle defects develop with a characteristic nasal step: The arcuate bundle defect extends to the nasal horizontal raphe to form a step-like configuration on kinetic visual field testing. The papillomacular bundle and vision are spared until late in the disease (HARRISON'S PRINCIPLES OF INTERNAL MEDICINE, 13$^{th}$ ed. Ed. By Isselbacher, Braunwald, Wilson, Martin, Fauci and Kasper. McGraw-Hill, New York City, 1996. Pp. 104–6). Intraocular pressure reflects the balance between the production and outflow of aqueous humor. The normal range for measurements by applanation tonometry (the tonometer applanates the corneal surface) is 2.09±2.5 mmHg. Another method of measuring intraocular pressure is briefly indenting the cornea with a Schiotz tonometer.

Glaucoma has a number of different etiologies. Glaucoma results from decreased outflow of fluid from the aqueous humor, the gel which occupies the intraocular space. The fluid does not properly drain through the pupil, trabecular meshwork, and Schlemm's canal and intraocular pressure rises. Open-angle or chronic glaucoma is the most common in adults. It is asymptomatic and only observed on a routine eye exam. There is a relative obstruction of the trabecular network of unknown cause. Treatment involves controlling intraocular pressure with topical agents including cholinergic (pilocarpine, carbachol, echothiophate) or adrenergic agonists (epinephrine dipivefrin) or antagonists such as β-adrenergic blockers including timolol, levobunalol and betaxolol. If topical agents do not reduce the intraocular pressure sufficiently, systemic carbonic anhydrase inhibitors such as acetazolamide or methazolamine are added. If medical therapy fails, surgery is tried, such as laser trabeculoplasty or filtration surgery, to improve aqueous outflow.

Open-angle or secondary glaucoma may occur in patients with ocular inflammatory or neoplastic disease, with mature cataracts. It also can occur with long-term topical or systemic glucocorticoid therapy.

Another form of glaucoma is called angle-closure glaucoma, which occurs when the iris blocks egress of aqueous humor through the trabecular meshwork. There is a primary form in which abnormal anatomy of the eye block drainage of the fluid through the pupil and the trabecular meshwork. The intraocular pressure rises suddenly whenever the pupil dilates. Symptoms include severe eye and face pain, nausea, vomiting, colored halos around lights, and loss of vision. Common signs are hyperemia, corneal edema and a fixed mid-dilated pupil. The intraocular pressure must be reduced urgently and is accomplished with hyperosmotic agents, including oral glycerin and sorbitol or intravenous mannitol. Acute angle-closure glaucoma is often treated with laser or surgical iridotomy.

Secondary angle-closure glaucoma occurs when the lens or ciliary body becomes swollen, pushing the iris against the trabecular meshwork or sealing the iris to the trabecular meshwork as a result of the formation of a neovascular network. This may occur in patients with diabetic retinopathy, advanced ocular ischemic syndrome due to severe occlusive carotid disease or inflammatory adhesions (synechiae) which can occur after iritis.

Compression of the optic nerve causes insidious progressive vision loss and visual field loss. The disc may be normal, swollen or atrophic. Intrinsic tumors which may compress the optic nerve include optic nerve sheath meningioma and glioma. In Graves' ophthalmopathy, optic neuropathy is due to compression of the nerve in the orbital apex by the enlarged extraocular muscles. Benign or malignant orbital tumors, metastatic lesions, tumors arising from the adjacent paranasal sinuses and middle cranial fossa and giant pituitary adenomas can each lead to compressive optic neuropathy.

Vision may be lost if papilledema is not promptly treated. Papilledema is swelling of the optic nerve head due to increased intracranial pressure. It is usually bilateral and occurs with brain tumors and abscesses, cerebral trauma and hemorrhage, meningitis, arachnoidal adhesions, pseudotumor cerebri, cavernous sinus thrombosis, dural sinus thrombosis, encephalitis, space-occupying brain lesions, severe hypertensive disease and pulmonary emphysema.

Vision also can be lost due to higher visual pathway lesions. The retinal nerves gather into the optic nerve, which may be impinged on in its pathway to the optic chiasma. At the optic chiasma the optic nerve fibers from the medial halves of both retina cross to the opposite side before connecting to the occipital visual cortex. Lesions at the optic chiasma tend to cause bilateral vision loss. Lesions at the visual cortex cause vision loss in the portions of the two retinas which are on the same side as the cortical lesion. Thus, vision is vulnerable to a number of different pathologies in a variety of intracranial locations.

Even if the patient obtains appropriate treatment, treatment today is limited to stopping further progression of vision loss, not improving vision. Because the patient may have already lost so much peripheral vision that he is effectively blind, the patient may not be permitted to drive, which may cause loss of job and independence, resulting in important deterioration in productivity and quality of life. A method of restoring at least some of the vision to enable the patient to return to work and other activities is sorely needed.

Because glaucoma and related conditions represent loss of central nervous neurons, it is appropriate to consider animal models of the treatment of central nerve damage, such as the neurotoxic Huntington's Disease (HD) model and the middle cerebral artery (MCA) stroke model.

Neural transplantation has been tried as a therapy in several animal models of Parkinson's disease and other neurodegenerative disorders (Bjorklund and Stenevi, Brain Res. 177:555–60, 1979; Sanberg et al., CELL TRANSPLANTATION FOR HUNTINGTON'S DISEASE, R. G. Landes Company, Austin Tex., 1994, p 124). This experimental treatment has been applied clinically in Parkinson's disease (PD) with favorable results (Lindvall et al., Science 247:574–77, 1990; Kordower et al., New Engl. J. Med. 332:1118–24, 1995; Freeman et al., Ann. Neurol. 38:379–88, 1995). Recently preliminary clinical trials of neural transplantation in HD also were conducted (Kurth et al., Amer. Soc. Neurol. Transplant. Abstr. 3:15, 1996). Previous studies on animal models of HD using neurotoxins (Sanberg et al., Prog. Brain Res. 82: 427–431, 1990; Borlongan et al., Brain Res. 697:254–57, 1995a; Borlongan et al., Brain Res. Bull. 36:549–56, 1995b) revealed selective lesions in the striatum, the brain area implicated in HD. Subsequent transplantation of neural cells in these neurotoxic HD models led to anatomical and behavioral recovery (Isacson et al., Neuroscience 22:481–97, 1987; Wictorin et al., Neuroscience 37:301–15, 1990; Borlongan et al., Restorative Neurol. Neurosci. 9:15–19, 1995c; and Pundt et al., Brain Res. Bull. 39:23–32, 1996).

Because of the similar brain damage in neurotoxic HD models and the MCA model, same-species fetal neural transplantation has been tested in ischemia (Nishino et al. 1993, ibid.; Koide et al., Restorative Neurol. Neurosci. 5:205–14, 1993; and Aihara et al., Brain Res. Bull. 33:483–88, 1993). Nishino et al. disclosed the effects of fetal rat striatal cell transplants in ischemic rats on a passive avoidance learning and memory task. Control animals acquired this task with minimal training, while ischemic animals had a marked and persistent impairment in acquiring this task. If ischemic rats received fetal striatal cell transplants two weeks after their surgery, the rats partially improved the ischemia-induced deficit in passive avoidance behavior. This improvement was observed at one month and extended throughout the three-month post-transplant test period. While these preliminary results are encouraging, they need to be replicated, and cognitive and locomotor alterations need to be evaluated. In general, rat fetal striatal cells grafted into the ischemic rat striatum significantly alleviated the chemical and behavioral deficits (See Borlongan et al., Neurosci. Biohav. Rev. 21:79–90, 1997). These results suggest that fetal neural transplantation may be beneficial in treating transient, focal cerebral ischemia.

However, logistical and ethical problems hinder widespread use of human fetal issue for human neural transplantation (Borlongan et al., Neurolog. Res. 18:297–304, 1996b). Alternative graft sources have been explored, such as encapsulated cells and genetically engineered cells (Emerich et al., 1996, ibid.; Kawaja et al., J. Neurosci. 12:2849–64, 1992). However, there is a need to develop cell lines that generate large numbers of differentiated or post-mitotic cells for human transplantation therapies (Mantione et al., Brain Res. Bull. 671:33–337, 1995). Recently we have transplanted treated cultured human neuronal cells (NT-2-Neuron cells derived from an embryonal cell line isolated from a human teratocarcinoma (Ntera2 or NT-2/D1™ cells) into the rodent brain (Kleppner et al., J. Comp. Neurol. 357:618–32, 1995; Miyazono et al., Brain Pathol. 4:575, 1994; Trojanowski et al., Exp. Neurol. 122:283–94, 1993). After retinoic acid treatment, NT-2/D1 cells differentiated into post-mitotic neuron-like (hNT-Neuron™) cells (Pleasure et al., J. Neurosci. Res. 35:585–602, 1992). In vivo studies indicate that transplanted hNT-Neuron cells can survive, mature and integrate into host brain (Kleppner et al., 1995, ibid.; Mantione et al., 1995, ibid.; Trojanowski et al., 1993, ibid.). Transplanted rats have been observed for more than one year, during which none of the transplanted hNT-Neuron cells have reverted to a neoplastic state.

These features of human hNT-Neuron cells, coupled with the localized lesion of certain types of vision losses, provided the basis for investigating the effects of hNT-Neuron cell transplantation on vision loss.

SUMMARY OF DISCLOSURE

Vision loss in a mammal can be treated by administering an effective amount of hNT-NEURON cells after the vision loss is diagnosed.

In another embodiment, vision loss in a mammal is caused by glaucoma or pathology which compressed the optic nerves.

In another embodiment, vision loss is treated by injecting hNT-NEURON cells into the eye. Alternately, or additionally, hNT-NEURON cells are injected into the visual cortex. In yet another embodiment, the mammal is treated with an immunosuppressant drug.

In yet another embodiment, vision loss is due to optic nerve sheath meningioma and glioma, Graves' ophthalmopathy, benign or malignant orbital tumors, metastatic lesions, tumors arising from the adjacent paranasal sinuses or middle cranial fossa, giant pituitary adenomas, brain tumors or abscesses, cerebral trauma or hemorrhage, meningitis, arachnoidal adhesions, pseudotumor cerebri, cavernous sinus thrombosis, dural sinus thrombosis, encephalitis, space-occupying brain lesions, severe hypertensive disease, or pulmonary emphysema.

DESCRIPTION OF DRAWINGS

The following figures are related to the MCA stroke studies which served as an animal model for treating vision loss.

FIGS. 1(A–D) shows dosing results of passive avoidance acquisition testing at pre- and post-transplant times.

FIGS. 2(A–D) shows dosing results of passive avoidance retention testing at pre- and post-transplant times.

FIGS. 3(A–D) shows dosing results of motor symmetry testing at pre- and post-transplant times.

FIG. 4 shows pre-transplant passive avoidance acquisition (left), retention (middle) and elevated body swing test (right).

FIG. 5 shows one-month post-transplant passive avoidance acquisition.

FIG. 6 shows one-month post-transplant passive avoidance retention.

FIG. 7 shows two-month post-transplant passive avoidance acquisition.

FIG. 8 shows two-month post-transplant passive avoidance retention.

FIG. 9 shows three-month post-transplant passive avoidance acquisition.

FIG. 10 shows three-month post-transplant passive avoidance retention.

FIG. 11 shows across three-month post-transplant passive avoidance acquisition.

FIG. 12 shows across three-month post-transplant passive avoidance retention.

FIG. 13 shows one-month post-transplant motor asymmetry.

FIG. 14 shows two-month post-transplant motor asymmetry.

FIG. 15 shows three-month post-transplant motor asymmetry.

FIG. 16 shows across three-month post-transplant motor asymmetry.

FIG. 17 shows six-month post-transplant passive avoidance acquisition.

FIG. 18 shows six-month post-transplant passive avoidance retention.

FIG. 19 shows six-month post-transplant motor asymmetry.

DETAILED DESCRIPTION

The present invention arose out of an observation relating to the positive results reported in U.S. patent application Ser. No. 08/797,952, filed on even date and entitled "TROPHIC FACTOR FROM hNT-NEURON™ HUMAN NEURONAL CELLS TO TREAT NEUROLOGIC DISORDERS", invented by Paul Sanberg, Cesario Borlongan, and Gary Snable and having attorney docket no. HNT-01. These results are detailed in Examples 1 and 2 below. Briefly, the biological effects of transplanting cultured human neurons (HNT-NEURON cells) derived from a well characterized human embryonal carcinoma cell line into the brains of rats subjected to stroke-like ischemic injury were investigated. The rat stroke model is characterized by transient, focal cerebral ischemia following embolic occlusion of the middle cerebral artery. At one month and extending throughout the 6-month post-transplantation test period, ischemic rats transplanted with HNT-NEURON cells and treated with immunosuppression displayed a significant improvement in a passive avoidance learning and memory task. Their asymmetrical motor behavior also normalized more than that of ischemic rats receiving rat fetal cerebellar cell transplantation or vehicle infusion. While ischemic rats given rat fetal striatal cells also exhibited significant behavioral improvement, HNT-NEURON transplanted animals showed more robust recovery at one month after transplantation. Ischemic animals receiving HNT-NEURON cells without immunosuppression showed significant behavioral recovery at one month after transplantation. Nevertheless, thereafter, behavior reverted to the post-ischemia levels that preceded transplantation. With monoclonal and polyclonal antibodies to the low-molecular-weight neurofilament protein as well as to human neural cell adhesion molecules, surviving HNT-NEURON cells were detected at 3 and 6 months after transplantation in immunosuppressed animals that displayed significant behavioral improvement. Thus, transplanted HNT-NEURON cells appeared to promote functional recovery. This supports the utility of HNT-NEURON cells as an alternative graft source for the treatment of transient, focal cerebral ischemia and possibly other neurodegenerative disorders.

Taking their findings a step further, because the transplanted hNT-Neuron cells grew and matured regardless of which brain tissue they encountered, I believe that there is another use for these cells. Because new nerves will grow down the same pathways which accommodated injured nerves, I believe that transplanting hNT-Neuron cells to the eye and/or visual cortex will be a useful method for treating blindness which is caused by glaucoma or other forms of optic nerve compression. Also, because the hNT-Neuron cells successfully replaced central nervous system nerves which are believed to die from excitotoxicity (GABA and glutamate-sensitive cells) and/or free radicals, I believe that the hNT neurons also will adequately replace retinal and optic nerves which also have GABA and glutamate receptors.

Definitions

"Impaired vision" or "vision loss" refers to the clinically observable signs and symptoms of loss of vision due to loss of retinal and/or central nervous system neurons. Impaired vision as used herein does not encompass near- or far-sightedness, presbyopia or cataracts which have other causes. Loss of vision is detectable by a variety of diagnostic tests and clinical observations which are well known in the medical profession. Such tests include visual field testing. In classical glaucoma, peripheral vision is lost. It may be discovered initially by auto-side-swiping accidents or by testing by a health care provider. Because the causes of vision loss are quite varied, the diagnostic methods likewise will be quite varied, but are well known in the health care profession and readily available in such references as HARRISON'S PRINCIPLES OF MEDICINE, ibid.

Examples of causes of loss of vision because of loss of central nervous system neurons include but are not limited to glaucoma, optic nerve sheath meningioma and glioma, Graves' ophthalmopathy, benign or malignant orbital tumors, metastatic lesions, tumors arising from the adjacent paranasal sinuses and middle cranial fossa, giant pituitary adenomas, brain tumors and abscesses, cerebral trauma and hemorrhage, meningitis, arachnoidal adhesions, pseudotumor cerebri, cavernous sinus thrombosis, dural sinus thrombosis, encephalitis, space-occupying brain lesions, severe hypertensive disease, and pulmonary emphysema.

"Beneficial effect" is an observable improvement over the baseline clinically observable signs and symptoms of vision loss. For example, a beneficial effect could include improvements in peripheral vision, if that were lost.

"Mammal" includes humans and other mammals who would reasonably benefit from treatment of stroke, including pets like dogs, cats and horses.

"NT-2/D1™ precursor cells" as used herein refers to a special cell line available from Layton Bioscience (Gilroy, Calif.). This cell line has been developed from a previously described human teratocarcinoma cell line (termed Ntera2/clone DI or NT2 cells) (Andrews et al. Lab. Invest. 50:147–162, 1981). These cells are precursors for hNT-Neuron™ human neuronal cells. NT-2/D1 cells are unique among other teratocarcinoma cell lines because these cells act like progenitor cells whose progeny are restricted to the neuronal lineage (Andrews, ibid.)

"hNT-Neuron human neuronal cells" as used herein refers to the special neuronal cell line disclosed in U.S. Pat. No. 5,175,103 to Lee et al. Briefly, NT-2/D1 precursor cells are induced to differentiate into neurons by administration of 10 $\mu$M retinoic acid which is replenished twice weekly for 5 weeks, after which the cells are replated three times with special manipulations to become more than 99% pure hNT-Neuron cells. The hNT-Neuron cells (also available from Layton Bioscience, Inc.) are research grade cells manufactured with antibiotics and were used in the subsequent experiments. Alternately, for human use, there is a cell line manufactured without antibiotics and under current good manufacturing practices (cGMP) which is termed LBS-Neurons™ human neuronal cells (Layton Bioscience, Inc.).

"Immunosuppressant" as used herein is a substance which prevents, attenuates and/or treats the host versus graft rejection which can occur when an allogenically different cell line or tissue is transplanted into a host. Examples of immunosuppressants include but are not limited to cyclosporine A, cyclophosphamide, and prednisone.

EXAMPLES

The MCA stroke model results are presented first. These are the same as reported in U.S. patent application Ser. No. 08/797,952, filed on even date and entitled "TROPHIC FACTOR FROM hNT-NEURON™ HUMAN NEURONAL CELLS TO TREAT NEUROLOGIC DISORDERS", invented by Paul Sanberg, Cesario Borlongan, and Gary Snable and having attorney docket no. HNT-01.

For Examples 1 and 2, Sprague-Dawley male rats (obtained from Zivic Miller) were used. All animals were free of virus antibody. A three-day acclimatization period was allowed prior to using the rats. Rats were kept under a 12–12-hour light/dark cycle and allowed free access to food and water before and after surgery. Particular care was taken to ensure that the rats were comfortable during surgery and in the recovery period. In the Example 2 study, 100 of the eight-week-old rats were introduced to ischemic or sham surgery at the start of the experiment. Twenty-three died during the surgery.

The MCA ischemic surgery was performed according to the method developed by Koizumi et al., Japan J. Stroke 8:1–8, 1986; and Nishino et al., 1993, ibid., with minor modifications (Borlongan et al., 1995b). Deeply anesthetized animals were placed in a supine position. After an incision at the neck, the junction between the internal and the external branches of the right carotid artery was exposed. An embolus, which measured 12–14 mm and was made by coating a 30 mm piece of 4.0 silk suture with silicone mixed with hardener, was then introduced through the external carotid artery and guided into the internal carotid artery. The embolus was positioned to block the origin of the right middle cerebral artery (MCA). The embolus was left in place for an hour and then removed. After removal of the embolus, the surgery was completed in less than five minutes. The cut in the external carotid artery was cauterized, and the incision of the muscles was sutured. Body temperature was kept normal with a heating pad until recovery.

For sham surgery, all procedures as stated above were followed except that no embolus was introduced into the external carotid artery.

Post-Ischemia Testing
Passive Avoidance Test

Rat training and testing were carried out using a step-down passive avoidance box (Lafayette Inst. Co.) according to a modified version of the methods described by Sanberg et al. (1978). The step-down apparatus was made of a 27×27×30 cm high Plexiglas® box with a 7.5×26.7 cm Plexiglas platform shelf located to the side of the box and 9.4 cm above the grid floor. Upon stepping off the platform, the rat received scrambled foot shock (approximately 2 mA, generated by a direct current shock scrambler BRS Foringer No. SCS-003) until running to the platform. Acquisition of avoidance was measured in terms of the amount of time required for the rat to learn to remain on the platform continuously for 3 minutes and the number of descents to the grid before the 3-min criterion was met "latency to step-down"). The acquisition tests at post-transplant times are considered relearning since the rats have encountered the same task previously. Retention measures the 24-hr memory of the task and does not involve electric shock. Retention was measured the day after the acquisition test by placing the rat on the platform exactly as before and recording the latency to step-down measured to a maximum of 3 min.

These tests were performed without the experimenter knowing the test group of the rats. Another individual coded the rats prior to placing them in the holding cages for transport to the testing apparatus and testing by a second individual. Previous studies (Borlongan et al., 1995d,e, ibid.) demonstrated that ischemic rats are impaired in both the acquisition and retention tasks of the passive avoidance test for over three months after ischemia surgery.

Motor Asymmetry (EBST)

The EBST was performed as described in detail by Borlongan and Sanberg, J. Neurosci. 15:5372–78, 1995. Briefly, the EBST involves suspending the rat by its tail and recording the number and direction of swings. The test apparatus is a clear Plexiglas box (40×40×35.5 cm) which was thoroughly cleaned with ethanol prior to each individual test of an animal. The animal was gently placed in the test apparatus with sufficient bedding to completely cover the bottom of the box and was allowed to move freely for two minutes to habituate within the box. The rat was then gently picked up at the base of its tail (approximately 1.5 inches from its body) and elevated by the tail until the animal's nose was about two inches (five cm) above the surface. The direction, either right or left, of the swing was counted once the rat's head moved laterally by approximately 10°, forming an angle to the body's midline. After a single swing, the animal was placed back in the Plexiglas box and allowed to move freely for 30 seconds prior to retesting. These steps were repeated 20 times for each rat, and the direction was recorded and tabulated. The EBST has previously been used to characterize the ipsilateral (to the lesion) biased swing activity of ischemic rats for three months after ischemia surgery (Borlongan et al., 1995d,e, ibid.).

Preparation of Cells for Transplantation

Rat fetal striatal cells, rat fetal cerebellar cells, hNT-Neuron cells (fresh or cryopreserved) or medium as described elsewhere in detail were used (Borlongan et al., 1995a, ibid.; Kleppner et al., 1995, ibid.; Mantione et al., 1995; Trojanowski et al., 1993, ibid.). Fresh and frozen hNT-Neuron cells were treated and prepared for cell transplantation as described previously (Kleppner et al., 1995, ibid.; Mantione et al., 1995, ibid.; Trojanowski et al., 1993, ibid.). Fresh hNT-Neuron cells were handled as follows: First, growth medium containing DMEM (high glucose), 10% (v/v) FBS and 2 mM glutamine was prepared. In a sterile area (e.g., a Class II biological safety cabinet), the surface of the T-25 tissue culture flask containing the hNT-Neuron cells was carefully wiped with 70% alcohol. The cap of the hNT-Neuron cell shipping container was removed. With a sterile Pasteur pipette, any remaining medium from the inside of the cap and the neck of the tissue culture flask was removed by aspiration. All of the shipping medium from the tissue culture flask was removed, and the culture was fed with 5 ml of Stratagene hNT-Neuron inhibitor medium. The flask was capped loosely. The cells were placed at 37° C. under 6% $CO_2$ in a humidified incubator. The medium was replaced with fresh 5 ml of hNT neuron inhibitor medium (Stratagene) at three days after receipt. On day 6 after receipt, the hNT neuron inhibitor medium was replaced with hNT neuron conditioned medium (Stratagene). On day 9 after receipt, the medium was charged with 5 ml fresh Stratagene hNT neuron conditioned medium. On day 12 after receipt, the transplantation was carried out.

On the day of transplantation, the hNT-Neuron cells were prepared as follows:
1. The cells were washed twice with PBS+$Ca^{2+}$+$Mg^{2+}$.
2. A solution consisting of 0.5 ml of a 0.025% (v/v) trypsin and 0.01% (w/v) EDTA solution in PBS (without the calcium and magnesium supplements)/25 $cm^3$ was added. The trypsin and EDTA solution was distributed evenly over the cell monolayer by swirling the flask. The flask was incubated for two minutes at room temperature. At this time, the neurons lifted off the monolayer.
3. The trypsinization process was stopped by adding 5 ml of Stratagene hNT-Neuron conditioned medium containing 10% (v/v) FBS.
4. Pasteur pipette with pipette aid were used to draw up cells and medium 2–3 times.
5. The cell solution was spun at 300×g for 10 minutes at room temperature.
6. The supernatant was removed with Pasteur pipettes, leaving the cell pellet at the bottom of the tube.
7. With a pipette aid, 0.1 ml of fresh hNT neuron conditioned medium was added.
8. A 10 $\mu$l sample was removed for viability cell count.
9. The remaining sample was transferred into a sterile microvial via sterile pipette. This cell solution was used for transplantation.

For cryopreserved hNT-Neuron cells, the same procedure as above was used on the day of transplantation; however, the cells were treated differently when they were received from Layton Bioscience, as described next:
1. Growth medium containing DMEM (high glucose), 10% (v/v) FBS, and 2 mM glutamine was prepared.
2. In a 37° C. water bath the cells in their shipping cryovial were thawed rapidly. The vial was flicked to gently resuspend the cells.
3. Ten ml of the Stratagene hNT-Neuron conditioned medium was pipetted into a sterile conical tube.
4. In a sterile area (e.g., a Class II biological safety cabinet), the surface of the cryovial was carefully wiped with 70% alcohol. The cells were transferred to the conical tube with a sterile pipette and mixed gently.
5. The cell suspension was spun at 300×g for 10 minutes.
6. Steps 6–9 for fresh hNT-Neuron cells were followed.

Immediately before and after hNT-Neuron cell transplantation, viability cell counts were performed by the trypan blue exclusion method and revealed at least 95% survival rate for both fresh and cryopreserved hNT-Neuron cells. Further cell counts based on the 3 $\mu$l infusion dosage revealed that, on the average, $7.8\times10^4$ and $2.3\times10^4$ cells were contained in each injection for fresh and cryopreserved hNT-Neuron cells, respectively.

Fetal rat striatal cells were obtained by dissecting the striatal lateral eminence of 16-day gestational age rats according to the procedures described by Pakzaban et al., Hum. Gene Ther. 5:987–95, 1994. Briefly, the dissected tissue pieces were first enzymatically (with trypsin) and then mechanically (with sterile pipette) dissociated into a cell suspension. Approximately two striatal anlages were in each transplantation dose, which corresponded to at least $8\times10^5$ viable cells.

Fetal rat cerebellar cells were obtained from the cerebellum of the same donors as striatal tissues (16-day gestational age) by dissecting out and enzymatically and mechanically dissociating the cells into cell suspension. Approximately the same number of fetal cerebellar cells as fetal striatal cells were in each dose ($8\times10^5$) by adjustment of the ratio of cerebellar cells and volume of medium.

The medium used for sham transplantation and fetal striatal and cerebellar cell suspensions was the standard "hibernation medium" (containing gentamycin) typically used for storing fetal cells (Freeman and Kordower, "Human cadaver embryonic substantia nigra grafts: effects of ontogeny, preoperative graft preparation and tissue storage." In: Lindvall, O., Bjorklund A., Widner, H., Eds., Elsevier Science Publishers, New York City, 1991, pp. 163–69).

Transplantation Procedure

All transplantation procedures were done under aseptic conditions. The animal was first anesthetized with sodium pentobarbital (70 mg/kg, intraperitoneally) and mounted in a Kopf (Tujunga, Calif.) stereotaxic frame (tooth bar=–2.5 mm). The incision site was shaved thoroughly and cleaned with Betadine® disinfecting solution. An approximately 0.75 inch incision was made through the skin on the superior portion of the rat's head. The overlying fascia was cleaned away with cotton swabs to clearly expose bregma. An initial reading of bregma coordinates was taken using the stereotaxic atlas (Paxinos and Watson, 1985). The transplant material (cells or medium) was then injected using a 25-gauge Hamilton syringe into the right striatum (AP=+1.2; ML=+2.6; DV=–6.0, from the bregma as taught by Paxinos and Watson (1985). Each rat received a 3 $\mu$l injection over a three-minute period. The Hamilton syringe was left in place for an additional five minutes before removal.

Following transplantation, rats were placed under heat lamps in autoclaved cages to avoid hypothermia. When the rats regained consciousness, the lamps were turned off, and the rats were carefully observed for any signs of complications. If the rat showed a significant weight loss after surgery, the rat was given lactated Ringer's solution and crushed food. Daily weights were recorded. In addition, each rat was observed for ambulation and grooming activity in its home cage. Any visible signs of infections of their eyes, paws and other body parts were also noted.

Post-Transplantation Observation

The weights of all rats were recorded daily, and the ambulation and grooming activity of each rat also were monitored while each animal was in its home cage.

Example 1

This study was performed to investigate the minimum effective dose of cryopreserved hNT cells that would product significant behavioral recovery in ischemic rats. Transplantation was carried out at one month after ischemic surgery. Ischemic rats were tested in motor asymmetry and passive avoidance learning task at one month after ischemic surgery. Only animals that displayed significant behavioral deficits were used as subjects and transplanted with specific doses (6–8 per group). In addition to a control group (seven received only vehicle), rats were given four different doses of cryopreserved hNT neurons in 3 $\mu$l injections: N40 ($4\times10^4$ cells); N20 ($2\times10^4$ cells); N10 ($1\times10^4$ cells); and N05 ($0.5\times10^4$ cells). All animals were immunosuppressed throughout the 3-month post-transplant period with cyclosporine-A (CsA; i.p. 10 mg/kg). At one, two and three months after transplant, all animals were tested in EBST and passive avoidance. At the end of the study, all animals were sacrificed for histological examination.

Cryopreserved hNT-Neuron human neuronal cells were received from Stratagene and used the same day according to the following procedure:
1. PBS (without calcium and magnesium supplements)/25 $cm^2$ was prepared.
2. The cells were thawed rapidly in a 37° C. water bath. The cryovial was flicked to gently resuspend the cells.

3. Ten ml of the prepared PBS was pipetted into a sterile conical tube.
4. In a sterile area (e.g., a Class II biological safety cabinet), the surface of the cryovial was carefully wiped with 70% alcohol. The cells were transferred to the conical tube with a sterile pipet and mixed gently.
5. The cell suspension was spun at 300×g for 10 minutes.
6. The supernatant was removed using Pasteur pipettes, leaving the cell pellet at the bottom of the tube.
7. Using a pipette aid, 0.1 ml of fresh PBS was added.
8. A 10 $\mu$l sample for aliquot was taken for cell count viability.
9. The remaining sample was transferred into a sterile microvial using a sterile pipette. This cell solution was used for transplantation.
10. Based on cell count viability, further dilution with PBS was then conducted to attain the final dosage of 0.5, 1, 2 and 4×10 hNT neurons.

Cell viability counts for the N05 dose were 84.89% and 46.5% for pre- and post-transplantation, respectively. For the dosage of N10, the viability counts were 83.7% and 35.8% for pre- and post-transplantation, respectively. For the dosage of N20, the viability counts were 80.6% and 69%, respectively. For the N40 dose, the viability counts were 86.9% and 52%, respectively. In general, animals did not exhibit any significant weight loss at post-ischemia and post-transplantation. However, five animals had significant weight loss associated with tumors of the neck and nape region (apparently not related to the transplant or transplant site). It is believed that the tumors were caused by chronic Cyclosporine-A injections, and this will be verified histologically.

FIGS. 1 and 2 show the results of passive avoidance acquisition and retention, respectively, in the five groups. At the pre-transplant time, all animals demonstrated significant impairment in their passive avoidance behavior (FIGS. 1A and 2A). At post-transplant (FIGS. 1B–D and 2B–D), the N40 group consistently displayed significant recovery in their acquisition and retention of the task compared to the medium-infused, N10 and N05 groups (p<0.05). The N20 group demonstrated significant recovery in their acquisition behavior compared to medium-infused and N05 groups at one and three months post-transplantation (p<0.05). The N20 group also displayed significant recovery in their retention of the task compared to medium-infused animals at three months post-transplantation (p<0.05). While the N10 and N05 groups did not exhibit significant recovery in their passive avoidance behavior, a trend of increasing retention time (FIGS. 2A–D) as well as decreasing acquisition time (FIGS. 1A–D) was noted in these groups as compared to medium-infused animals across the post-transplantation period FIG. 3 shows the results of motor symmetry testing (EBST). At pre-transplant, no group significantly differed in their biased swing behavior (FIG. 3A). At post-transplant period (FIGS. 3B–D), animals receiving the N40 dose consistently displayed significant normalization in their behavior compared to the medium-infused, N05 and N10 groups (p<0.05). While animals in the N05 and N10 groups did not exhibit significant recovery in their biased swing behavior, a trend of reduced ipsilateral biased swing behavior was noted in these groups compared to medium-infused animals across the post-transplantation period.

These data show that the minimum effective dose that significantly corrected behavior deficits was 4×10$^4$ cells. At some time after transplant, the dosage of 2×10$^4$ cells also caused significant improvement. Of note, the data from the five animals with tumors were included for analyses of one- and two-month data. Examination of the data from the animals with tumors revealed that their performances in both avoidance tests significantly deviated from their group mean. When the animals died and were therefore unavailable for three-month testing, the data from the N20 group revealed a significant increase in passive avoidance retention (FIG. 2D) compared to the medium-treated group. Based on this analysis the efficacy of the 2×10$^4$ cell dose cannot be ruled out.

Example 2

In this study, rats were administered not only fresh and cryopreserved hNT-Neuron cells but also rat fetal cells as positive and negative controls. One month after stroke surgery, animals that showed significant behavioral deficits compared to control sham or normal animals were randomly assigned to stroke-surgery transplant groups. They were transplanted with (1) rat fetal striatal cells, (2) rat fetal cerebellar cells, (3) hNT-Neuron cells (fresh or cryopreserved, with or without cyclosporine (CsA) treatment), or (4) medium as described in detail elsewhere (Borlongan et al., 1995a, ibid.; Kleppner et al., 1995, ibid.; Mantione et al., 1995, ibid.; Trojanowski et al., 1993, ibid.). Additional animals (normal and sham-surgery rats) were added to serve as controls. The study groups also included controls of the two surgical procedures (stroke and transplantation) and are summarized in the following table:

| Group 1 | Normal animals (n = 2) |
| Group 2 | Sham-surgery/medium infusion (n = 6) |
| Group 3 | Stroke-surgery/medium infusion (n = 8) |
| Group 4 | Sham-surgery/striatal cell transplant (n = 4) |
| Group 5 | Stroke-surgery/striatal cell transplant (n = 8) |
| Group 6 | Stroke-surgery/cerebellar cell transplant (n = 6) |
| Group 7 | Stroke-surgery/fresh hNT-Neuron cell transplant + CsA (n = 14) |
| Group 8 | Stroke-surgery/cryopreserved hNT-Neuron cells + CsA (n = 14) |
| Group 9 | Stroke-surgery/fresh hNT-Neuron cells (no CsA) (n = 6) |
| Group 10 | Stroke-surgery/CsA treatment only (n = 8) |

Selected rats were also immunosuppressed with Cyclosporine (CsA) (Sandoz) which was given by intraperitoneal injection at a dose of 10 mg/kg/day, starting on the day of transplantation and lasting until date of sacrifice. The CsA was obtained in liquid form, dissolved in olive oil (the vehicle, also supplied by Sandoz) at a concentration of 50 mg/kg.

Post-Ischemic Surgery Test

One month after surgery, rats were tested for passive avoidance behavior and asymmetric motor behavior as described above. FIG. 4 shows results for passive avoidance acquisition behavior (left panel). Retention (middle panel), and elevated body swing EBST; right panel). Ischemic animals showed deficits in acquisition and retention of passive avoidance task compared to sham and normal controls (p<0.00001).

Post-Transplantation Observation and Testing

No visible signs of infections (e.g., in the eyes, paws, skin, etc.) were noted except in one animal. This one was the only of 77 rats that received a graft and died, and this occurred three weeks after transplant. This rat had received rat fetal cerebellar cells and showed significant weight loss, poor grooming activity and an eye infection. At necropsy, the rat had a brain tumor in the vicinity of the transplant. Aside from this rat, all other animals showed similar weight gains, ambulation and grooming activity for six months after transplant.

The rats treated with CsA were noticeably more active (i.e., they displayed more vocalizations and movements) than the rats receiving no CsA. This observation is consistent with earlier reports that CsA induces an increase in general spontaneous locomotor activity in normal rats (Borlongan et al., Cell Transplant 1:65–73, 1995f) as well as in Parkinsonian rats (Borlongan et al., 1996c, ibid.).

At 1, 2, 3 and 6 months after transplantation, rats were again evaluated on the behavioral tests. All tests were run blind, and the animal codes were revealed only at the end of the 6-month period.

In general, behavioral data from both the passive avoidance test and EBST demonstrated that striatally mediated learning and memory task and motor behavior, which were impaired by the ischemic insult, were improved by the transplantation of hNT-Neuron cells and fetal striatal cells. Immunosuppression after the hNT-Neuron cell transplant prolonged the behavioral improvement associated with the hNT-Neuron cells.

The data were analyzed statistically by the analysis of variance (ANOVA) technique with surgical procedure (sham versus ischemic surgery), grafted cell and treatment specificity, and time periods (1, 2, 3 and 6 months after graft) as factors were conducted for motor asymmetry passive avoidance behavior at pre- and post-graft dates. Preliminary tests for homogeneity of variance were conducted. Preplanned orthogonal comparisons among groups were performed.

At one month after transplantation, there was a significant recovery of both the acquisition (FIG. 5) and retention (FIG. 6) of passive avoidance in recipients of hNT-Neuron cells and rat fetal striatal cells ($p<0.0001$). This behavioral recovery continued throughout the six months post-transplant interval, except in those animals transplanted with hNT-Neuron cells but not given CsA. The hNT-Neuron/no CsA group showed less behavioral recovery starting two months after graft (FIGS. 7–19), particularly compared to rats receiving both hNT-Neuron cells and CsA ($p<0.00001$). However, the hNT-Neuron/no CsA group still showed a significant behavioral recovery compared to rats receiving fetal cerebellar cell grafts or medium alone at the later post-transplant periods ($p<0.05$).

For the elevated body swing test (EBST), results also are shown in FIG. 4. The results mirror those in the passive avoidance test. All animals receiving hNT-Neuron cells and fetal striatal cells showed behavioral recovery in the EBST throughout the six month post transplant period ($p<0.00001$). Even the hNT-Neuron/no CsA group displayed normalization of their swing activity at one month after graft (FIG. 13); however, this recovery was not sustained at later time points. In sharp contrast, control ischemic animals receiving either rat fetal cerebellar cell grafts or medium alone had no improvement at any time in their EBST.

Post-Mortem Results

In all, the brains of 54 rats were available for neuropathologic examination and immunohistochemical analysis. Post-mortem studies (like the other tests) were done without access to any information concerning the transplant groups. The rat brains were immersion-fixed with 70% ethanol with 150 mM NaCl for two to three days and were processed for histologic and immunohistochemical study after paraffin embedding. Coronal sections (6 μm thick) were prepared from coronal slabs of the paraffin-embedded brains, and 200 to 450 serial sections were obtained through the brains. On every tenth section, hematoxylin and eosin (H&E) and immunohistochemical staining (see Table 1) were done. Perl's Prussian Blue stain for ferric iron (i.e., to detect hemosiderin from focal hemorrhage in the needle track for the graft) also was employed to confirm the location of the needle track and graft site in all cases.

The needle track and injection site were identified in 48 rat brains, and most rat brains showed evidence of focal hemorrhage. Although the deepest extent of the injection sites varied, the injection site was located in the caudatoputamen in 35 brains, while the injection site in the other 13 brains was in the white matter immediately dorsal to the caudatoputamen. However, in the remaining six cases (rats numbered 23, 25, 26, 27, 29 and 30), the injection site or needle track could not be detected, even after extensive analysis of serial sections of the caudatoputamen stained by H&E and Prussian Blue methods as well as by immunohistochemistry using the panel of antibodies described below. After the code was broken at the end of the study, these six cases were determined to be control stroked animals that received CsA treatment alone, without any transplantation.

The methods used for the light microscope immunohistochemical studies conducted on paraffin sections were essentially the same as those described elsewhere (Trojanowski, et al., Amer. J. Pathol. 135:747–58, 1989; Kleppner et al., 1995; Miyazono et al., 1995). Briefly, deparaffinized sections of the rat brain were incubated in the primary antibody overnight. The bound antibody was visualized using a peroxidase anti-peroxidase (PAP) or avidin biotin complex (ABC) method in conjunction with diamino benzidine (DAB) as the chromogen.

Both monoclonal (Mabs) and polyclonal antibodies to low-molecular-weight neuronal cytoskeletal filament protein (NFL) as well as to N-CAM polypeptide were used to identify and characterize the phenotype of the graft cells and maturation of the grafts.

Immunohistochemistry for glial fibrillary acid protein (GFAP) was employed to highlight gliosis surrounding the needle track in order to identify the deepest extent of the graft. The properties of these antibodies have been characterized and used extensively in previous transplantation studies of humans and experimental animals.

Immunochemistry for N-CAM and NFL was performed on all 48 cases in which the needle track was identified in H&E, GFAP and/or Prussian Blue stained sections. Since the Mab MOC-1 recognizes human specific epitope in N-CAM, and it does not cross react with rodent N-CAM or other rodent proteins, MOC-is highly effective in detecting grafted hNT-Neuron cells in the rat brain (Trojanowski et al., 1993). Rats with hNT-Neuron grafts were positively stained with MOC-1. Most cases showed N-CAM-positive hNT-Neuron cells in the most ventral segment of the needle track; however, grafted cells also extended into the adjacent brain in nine cases (#45, 52, 53, 56, 75, 80, 81, 91, and 94). Of the 33 animals receiving hNT-Neuron grafts, 24 cases positively stained with MOC-1. Of the nine non-staining cases, six were in the hNT-Neuron/no CsA group, in whom the hNT-Neuron cells may no longer have been present. In the other three cases, grafted hNT-Neuron cells were not very positively stained for MOC-1; and in one case, the hNT-Neuron cell graft was in the lateral ventricle. The two other cases revealed very small grafts that were stained equivocally or not at all for MOC-1. These small grafts might have been negative due to the low number of injected hNT-Neuron cells.

On the other hand, the anti-NFL antiserum (a-NFL) labeled cells in the surviving transplants regardless of whether or not they were positive for both N-CAM and NFL; whereas, rat striatal and cerebellar neuronal transplants were positive only for NFL. The a-NFL antibody identified grafted neurons in 30 cases including 18 grafts that also were positive for N-CAM (i.e., hNT-Neuron cells). For four grafts which extended into the white matter surrounding the caudatoputamen, the cytoplasm of the grafted cells showed an intensively positive reaction for NFL and N-CAM in three cases (#45, 52, and 91), and another case (#94) showed a bundle of processes that were positive for both proteins. Twelve cases were positive for NFL alone, while 11 cases did not stain for any of these proteins.

Gross morphologic examinations revealed no evidence of difference in cell survival between three months and six months transplant maturation of either hNT-Neuron cell grafts with immunosuppression or fetal striatal cells.

Rats showing good behavioral recovery (within two standard deviations of the mean) were selected for histological analysis at three months after transplantation. The remaining animals were evaluated by the same behavioral tests for up to 6 months after transplantation to determine any long-term behavioral recovery. Additional animals (Group 5, n=1; Group 6, n=1; Group 7, n=7; Group 8, n=7; Group 9, n=4) sacrificed for similar immunohistochemical analyses of the grafts at six months after transplantation.

Needle tracks stained positively by hematoxylin and eosin (H&E) had accompanying hemosiderin brown deposits. Gliosis surrounded needle tracks, as indicated by the anti-GFAP MAb (2.2B10). An hNT-Neuron cell graft was positively stained by the MOC-1 MAb specific for human N-CAM. hNT-Neuron cells with neuron-like features were stained by the anti-NFL. Rat neuronal transplants also were positive for NFL, but they we negative for human N-CAM, as was the host brain.

Ischemia-induced dysfunction in passive avoidance learning and memory and in asymmetrical motor behavior was significantly corrected in rats given hNT-Neuron cell grafts with or without CsA. Importantly, this behavioral recovery was seen as early as one month post graft, and the recovery persisted throughout the entire six month recovery period. Recovery was best at six months for hNT-Neuron rats receiving CsA. Because these rats had surviving hNT-Neuron cells, the hNT-Neuron grafts are believed to be responsible for the long-term improvements in the ischemia-induced behavioral deficits initially observed in the test rats. Rats receiving hNT-Neuron grafts but no CsA had essentially no visible graft cells and less improvement at six months. The present observation that grafted hNT-Neuron human neuron-like cells promote recovery from ischemia-induced behavioral deficits agrees with earlier reports showing that grafts of fetal striatal cells implanted into the caudatoputamen partially restore functions impaired by ischemia damage to the striatum (Aihara et al., 1993, ibid.; Nishino et al., 1993, ibid.; Koide et al., 1993, ibid.). All three groups of hNT-Neuron grafted rats demonstrated recovery of function. While the immunosuppressed animals receiving hNT-Neuron cells maintained their recovery for the 6 month study, the recovery in the non-immunosuppressed hNT-Neuron graft recipients decreased at about two months after the transplant. However, the magnitude of the behavioral recovery produced by hNT-Neuron grafts in rats not receiving CsA was greater than that seen in stroke rats that received cerebellar cells, medium alone or CsA alone.

Chronic immunosuppressive therapy as an adjunct to hNT-Neuron cell graft in rats was associated with optimal and sustained functional improvement and prolonged graft survival. The near absence of visible grafts in the hNT-Neuron/no CsA group probably results from the immunological rejection of these grafts. Nonetheless, the hNT-Neuron/no CsA group was significantly improved compared to stroke rats receiving fetal cerebellar or medium grafts or no graft but CsA therapy. These data suggest that the trophic effects of the transplanted hNT-Neuron cells are sustained for a prolonged period after transplant in non-immunosuppressed animals. Nevertheless, immunosuppression with CsA enhanced the survival of hNT-Neuron grafts, which is consistent with study of the transplantation of hNT-Neuron cells into adult and neonatal rat brains (Trojanowski et al., 1993, ibid.).

Surviving hNT-Neuron cells were detected in otherwise healthy, functioning rats for the entire six month recovery period. These data are consistent with previous publications which concluded that there was no evidence to suggest that transplanted hNT-Neuron cells have any deleterious effects on the host brain (Miyazono et al., 1994, ibid.; Kleppner et al., 1995, ibid.; Mantione et al., 1994, ibid.).

While behavioral recovery was observed in rats receiving fetal striatal grafts, all hNT-Neuron transplanted groups (with and without CsA) showed a more robust recovery at one month after graft. For example, while the fetal striatal group improved its passive avoidance acquisition time by 84 seconds, all hNT-Neuron groups showed improvements in excess of 150 seconds. Since there has been no reported evidence that neural transplants replace lost brain tissue at one month (Bankiewicz et al., 1993; Borlongan et al., 1996d), the improved function is likely to be due to trophic factor(s) from the grafted hNT-Neuron cells. Accordingly, the human-derived hNT-Neuron cells released at least one hNT trophic factor that ameliorates ischemic deficits better than those from fetal striatal cells. Of note, fewer hNT-Neuron cells were grafted (an average of $7.8 \times 10^4$ and $2.3 \times 10^4$ cells per injection of fresh and cryopreserved hNT-Neuron cells, respectively), compared to fetal striatal cells (about $8 \times 10^5$ cells).

In conclusion, the speedier recovery observed in rats receiving hNT-Neuron cells (with and without cyclosporine) and the continued improved function of rats receiving hNT-Neuron cells without cyclosporine in spite of microscopic evidence of few or no remaining hNT-Neuron cells indicates that at least one neurotrophic factor was provided by the hNT-Neuron cells and that factor has a significant long term effect on mammalian stroke recovery. The fact that recovery was slower initially and/or less with rat fetal striatal cells indicates that those cells produce less, different or none of the trophic factor(s) produced by the hNT-Neuron cells. These facts are all the more surprising when one considers that only one tenth the number of hNT-Neuron cells as of fetal rat striatal cells was transplanted.

The facts that (1) some of the hNT-Neuron cells survived in the white matter outside the intended graft site and (2) those animals improved like the other animals lend themselves to some interesting conclusions. In contrast to an earlier report that hNT-Neuron cells may become cancerous outside the intended graft site, these grafts remained functional and retained hNT-Neuron characteristics for the full study period, indicating that hNT-Neuron cells are beneficial and not harmful outside their intended graft site. Thus, hNT-Neuron cells can be considered to be pluripotent, in that they function among different parts of the brain. Thus hNT-Neuron cells and/or the trophic factor(s) can be used for stroke occurring in various parts of the brain.

In addition, the hNT-Neuron cells and/or hNT trophic factor(s) can be used to treat other neuronal disorders which are caused by the same mechanism as is stroke. According to Yatter et al (The Neuroscientist, 1:286–97, 1995), excitotoxicity and/or free radicals have been proposed to also play roles in neuronal damage in not only stroke but also in hypoglycemia, trauma, Huntington's disease, Parkinson's disease, Wernicke's encephalopathy, epilepsy and amytrophic lateral sclerosis (ALS). Although hNT-Neuron cells have not been transplanted into patients with any of these other diseases, such transplantation or administration of hNT neurotrophic factor(s) is likely to be helpful in overcoming the same mechanism of action and offering improved memory and learning, as observed in the ischemic rats.

Example 3

A dose study is disclosed for treatment of vision loss due to chemical retinal damage in rats. A small amount of caustic chemical is injected into one eye. After the eye heals, the eye is injected with one of several doses of hNT-Neuron cells. Some of the rats are controls, while others receive cyclosporine-A. Vision of the rats is tested at intervals after the transplant of hNT-Neuron cells. After a suitable interval, rats are sacrificed and histologic studies, as detailed above, are performed to observe the state of the transplanted hNT-Neuron cells. Assuming that a similar effect to that of Examples 1 and 2 is observed, a study of glaucomatous Beagles is contemplated next.

Example 4

A dose study is disclosed for treatment of vision loss due to glaucoma. Beagles which congenitally acquire glaucoma at about 12 to 18 months are maintained until they show significant signs and symptoms of loss of vision. The mature animals are divided into groups for dosing. Dosing is determined based on the number of ocular nerves which may need to be replaced. It has been estimated that humans lose as many as $5 \times 10^5$ nerve cells in glaucoma. Dosing is by injection into the eye of vehicle alone (control), $4 \times 10^4$, $8 \times 10^4$ and $12 \times 10^4$ cells per injection volume of 3 µl.

The ocular entry procedure is similar to procedures used by ophthalmologists to gain access to the retina and aqueous humor. Entry with a relatively narrow-gauge needle is made at a small sclerotomy incision and the tip of the needle is positioned in the retinal space. The injection volume is delivered slowly, over at least three minutes, to avoid retinal detachment. The needle is left in place for an additional five minutes to avoid letting nerve cells migrate away from the retina.

Alternately or additionally, each animal can be injected in the visual cortex at the dorsal surface of the brain. For peripheral vision losses, the visual cortex area is relatively small and can be located stereotaxically.

The test animals are observed for six months to two years to record vision improvements. At the end of the study, autopsies are performed. Special precautions are taken to assure that the eye and brain tissue are properly preserved to permit histological analysis of nerve growth. Anti-hNT antibodies are applied to the slides to distinguish the mature hNT-Neuron cells from the animals' own neurons.

The foregoing description and examples are intended only to illustrate, not limit, the disclosed invention.

I claim:

1. A method of replacing lost or injured ganglion cells in a mammal, said method comprising
    a) obtaining pluripotent human neuronal cells;
    b) centrifuging the cells to form a pellet and removing the supernatant;
    c) adding a diluent to resuspend the pelleted cells;
    d) transferring the resuspended cells to a syringe; and
    e) injecting an effective amount of the resuspended cells into a central nervous system location selected from the group consisting of the eye, the visual cortex, and the retina, thereby replacing lost or injured ganglion cells.

2. The method of claim 1 wherein said loss or injury of ganglion cells is caused by glaucoma.

3. The method of claim 1 wherein step e comprises injecting the resuspended cells into a mammal's eye.

4. The method of claim 1 wherein the mammal also is treated with an immunosuppressant drug.

5. The method of claim 4 wherein the immunosuppressant drug consists of cyclosporine A, cyclophosphamide, or prednisone.

6. The method of claim 1 wherein the loss of or injury to ganglion cells is caused by injuries and conditions which affect the eye, the optic nerve or both.

7. A method of treating the loss of or injury to ganglion cells in a mammal, the method comprising
    a) obtaining pluripotent human neuronal cells;
    b) centrifuging the cells to form a pellet and removing the supernatant;
    c) adding a diluent to the pelleted cells and resuspending the pelleted cells;
    d) transferring the resuspended cells to a syringe; and
    e) injecting an effective amount of the resuspended cells into an eye of the mammal,
    whereby the ganglion cells are replaced.

8. A method of replacing lost or injured ganglion cells in a mammal, said method comprising
    a) obtaining pluripotent human neuronal cells;
    b) centrifuging the cells to form a pellet and removing the supernatant;
    c) adding a diluent to resuspend the pelleted cells;
    d) and injecting an effective amount of the resuspended cells into at least two central nervous system locations where ganglion cells are lost or injured, wherein at least one of said locations is selected from the group consisting of an eye, the visual cortex, and the retina.

9. The method of claim 8 wherein the central nervous system locations are selected from at least one eye, visual cortex or a combination thereof.

* * * * *